United States Patent
Tsuji et al.

(10) Patent No.: US 11,714,043 B2
(45) Date of Patent: Aug. 1, 2023

(54) SPECIMEN ANALYSIS SYSTEM AND SPECIMEN ANALYSIS METHOD

(71) Applicant: SYSMEX CORPORATION, Kobe (JP)

(72) Inventors: Tomohiro Tsuji, Kobe (JP); Hiroo Tatsutani, Kobe (JP)

(73) Assignee: SYSMEX CORPORATION, Kobe (JP)

(*) Notice: Subject to any disclaimer, the term of this patent is extended or adjusted under 35 U.S.C. 154(b) by 807 days.

(21) Appl. No.: 16/579,901

(22) Filed: Sep. 24, 2019

(65) Prior Publication Data
US 2020/0096432 A1    Mar. 26, 2020

(30) Foreign Application Priority Data
Sep. 26, 2018 (JP) ................................. 2018-180025

(51) Int. Cl.
*G01N 15/14* (2006.01)
*G16H 10/40* (2018.01)

(52) U.S. Cl.
CPC ......... *G01N 15/1404* (2013.01); *G16H 10/40* (2018.01); *G01N 2015/1402* (2013.01); *G01N 2015/1493* (2013.01)

(58) Field of Classification Search
CPC ....... G01N 15/1404; G01N 2015/1402; G01N 2015/1493; G01N 2015/1006; G01N 15/1459; G01N 15/1434; G01N 15/1429; G16H 10/40
See application file for complete search history.

(56) References Cited

U.S. PATENT DOCUMENTS

| | | | |
|---|---|---|---|
| 8,176,409 B2* | 5/2012 | Novo | G06F 16/958 715/248 |
| 8,808,623 B2* | 8/2014 | Linssen | G16H 50/20 422/65 |
| 9,934,364 B1* | 4/2018 | Kumar | G06N 3/045 |

(Continued)

FOREIGN PATENT DOCUMENTS

| | | |
|---|---|---|
| EP | 2037281 A2 | 3/2009 |
| EP | 2037281 A3 | 8/2017 |

(Continued)

OTHER PUBLICATIONS

BD Facsuite Software, Retrieved from the Internet, URL: http://www.bdbiosciences.com/jp/instruments/software/facsuite/index.jsp, Retrieved on Sep. 2019, BD Biosciences; Cited in the Specification.

(Continued)

*Primary Examiner* — Roy M Punnoose
(74) *Attorney, Agent, or Firm* — Metrolex IP Law Group, PLLC

(57) ABSTRACT

A specimen analysis system includes: a measurement data acquisition unit that acquires measurement data of particles obtained from a flow cytometer measuring the particles contained in a measurement specimen prepared by adding a reagent to a sample; an output mode information acquisition unit that acquires output mode information indicating an output form of the measurement data; and an output unit configured to output the measurement data in the output form in accordance with the output mode information.

23 Claims, 9 Drawing Sheets

(56) References Cited

U.S. PATENT DOCUMENTS

| | | | |
|---|---|---|---|
| 2005/0123445 A1* | 6/2005 | Blecka | G01N 35/0099 422/64 |
| 2006/0148063 A1* | 7/2006 | Fauzzi | G01N 1/31 422/65 |
| 2007/0172388 A1* | 7/2007 | Padmanabhan | G01N 15/1404 422/400 |
| 2007/0179715 A1* | 8/2007 | Ariyoshi | G16H 10/40 702/19 |
| 2008/0228444 A1* | 9/2008 | Olson | G01N 15/1429 702/189 |
| 2009/0068062 A1* | 3/2009 | Jafari | G01N 1/38 436/179 |
| 2010/0101339 A1* | 4/2010 | Tatsutani | G01N 35/00584 73/863.91 |
| 2012/0109529 A1* | 5/2012 | Ariyoshi | G01N 35/00722 702/19 |
| 2013/0346023 A1* | 12/2013 | Novo | G01N 15/1429 702/179 |
| 2014/0093949 A1* | 4/2014 | Norton | G01N 15/1459 422/69 |
| 2018/0284008 A1* | 10/2018 | Kinishi | G01N 15/1425 |
| 2018/0285754 A1* | 10/2018 | Yao | G06N 5/045 |
| 2018/0348112 A1* | 12/2018 | Nagai | G01N 15/1459 |
| 2020/0098452 A1* | 3/2020 | Tatsutani | G01N 15/14 |

FOREIGN PATENT DOCUMENTS

| | | |
|---|---|---|
| JP | H10-282106 A | 10/1998 |
| JP | 2007-078508 A | 3/2007 |
| JP | 2009-036587 A | 2/2009 |
| JP | 2009-068979 A | 4/2009 |
| JP | 2009-174942 A | 8/2009 |
| JP | 2010-054517 A | 3/2010 |

OTHER PUBLICATIONS

Flow Cytometers, Retrieved from the Internet, URL: https://ls.beckmancoulter.co.jp/products/flow-cytometers/, Retrieved on Sep. 2019, Beckman Coulter; Cited in the Specification.

Extended European search report dated Feb. 24, 2020 in a counterpart European patent application.

Communication dated Feb. 23, 2022 in a counterpart European patent application.

Japanese Office Action dated May 12, 2022 in a counterpart Japanese patent application.

* cited by examiner

FIG. 4

MEASUREMENT CONDITION FILE INFORMATION

| No. | CLASSIFICATION(1) | CLASSIFICATION(2) | ITEM NAME |
|---|---|---|---|
| 1 | BASIC MEASUREMENT INFORMATION | BASIC INFORMATION | MEASUREMENT CONDITION ID |
| 2 | | | MEASUREMENT CONDITION NAME |
| 3 | | | COMMENT |
| 4 | | MEASUREMENT INFORMATION | ANALYSIS AMOUNT |
| 5 | | | FLOW RATE |
| 6 | | | DILUTION RATIO |
| 7 | | THRESHOLD | THRESHOLD(FSC) |
| 8 | | | THRESHOLD(SSC) |
| 9 | | | THRESHOLD(FL1) |
| 10 | | | THRESHOLD(FL2) |
| 11 | | | THRESHOLD(FL3) |
| 12 | | | THRESHOLD(FL4) |
| 13 | INFORMATION ON DETECTION SENSITIVITY ADJUSTMENT | AMPLIFICATION VALUE | AMPLIFICATION VALUE(FSC) |
| 14 | | | AMPLIFICATION VALUE(SSC) |
| 15 | | PMT VOLTAGE | PMT VOLTAGE VALUE(FL1) |
| 16 | | | PMT VOLTAGE VALUE(FL2) |
| 17 | | | PMT VOLTAGE VALUE(FL3) |
| 18 | | | PMT VOLTAGE VALUE(FL4) |
| 19 | INFORMATION ON OPTICAL INFORMATION CORRECTION | FLUORESCENCE CORRECTION VALUE | FLUORESCENCE CORRECTION VALUE(FL1-FL2) |
| 20 | | | FLUORESCENCE CORRECTION VALUE(FL1-FL3) |
| 21 | | | FLUORESCENCE CORRECTION VALUE(FL1-FL4) |
| 22 | | | FLUORESCENCE CORRECTION VALUE(FL2-FL1) |
| 23 | | | FLUORESCENCE CORRECTION VALUE(FL2-FL3) |
| 24 | | | FLUORESCENCE CORRECTION VALUE(FL2-FL4) |
| 25 | | | FLUORESCENCE CORRECTION VALUE(FL3-FL1) |
| 26 | | | FLUORESCENCE CORRECTION VALUE(FL3-FL2) |
| 27 | | | FLUORESCENCE CORRECTION VALUE(FL3-FL4) |
| 28 | | | FLUORESCENCE CORRECTION VALUE(FL4-FL1) |
| 29 | | | FLUORESCENCE CORRECTION VALUE(FL4-FL2) |
| 30 | | | FLUORESCENCE CORRECTION VALUE(FL4-FL3) |
| 31 | INFORMATION ON GATING | INFORMATION ON SCATTERGRAM | SCATTERGRAM NAME |
| 32 | | | HIGHER-LEVEL GATE |
| 33 | | | X-AXIS ch |
| 34 | | | X-AXIS ch NAME |
| 35 | | | X-AXIS ch |
| 36 | | | X-AXIS ch NAME |
| 37 | | INFORMATION ON HISTOGRAM | HISTOGRAM NAME |
| 38 | | | HIGHER-LEVEL GATE |
| 39 | | | X-AXIS ch |
| 40 | | | X-AXIS ch NAME |
| 41 | | INFORMATION ON GATE | GATE NAME |
| 42 | | | POSITION INFORMATION |
| 43 | | | COLOR |
| 44 | | | MEASUREMENT ITEM NAME |
| 45 | | | UPPER LIMIT VALUE |
| 46 | | | LOWER LIMIT VALUE |
| 47 | | | RESULT VALUE TYPE |
| 48 | TEMPERATURE CORRECTION FORMULA | | |

| PATIENT | PARENT SAMPLE | CHILD SAMPLE | REAGENT | ... |
|---|---|---|---|---|
| A | 0001 | 0001-1 | IVD | ... |
|  |  | 0001-2 | RUO | ... |
|  |  | 0001-3 | ASR | ... |
|  | ... | ... | ... | ... |
| B | 0001 | 0001-1 | IVD | ... |
|  | ... | ... | ... | ... |

SPECIMEN ANALYSIS SYSTEM AND SPECIMEN ANALYSIS METHOD

CROSS REFERENCE TO RELATED APPLICATIONS

This application claims priority from to prior Japanese Patent Application No. 2018-180025 filed with the Japan Patent Office on Sep. 26, 2018, the entire contents of which are incorporated herein by reference.

BACKGROUND

The present disclosure relates to a specimen analysis system and a specimen analysis method that use flow cytometry.

Flow cytometry is known as a method that optically detects the size, structure, fluorescence intensity, and the like of each of particles dispersed in a liquid by using a flow cytometer capable of detecting each of particles, and measures the number and distribution of the particles based on the detected information.

In a specimen analysis system using a flow cytometry, the format of a report including research use measurement data of particles contained in a measurement specimen prepared through addition of a research use only reagent (RUO reagent) to a sample can be freely changed by a user such as a doctor. On the other hand, the format of a report including clinical test use measurement data of particles contained in a measurement specimen prepared through addition of an in-vitro diagnostics reagent (IVD reagent) to a sample is predetermined by each company that provides a specimen analysis system using a flow cytometry, and a user is not allowed to freely change the format (the Internet <URL: http://www.bdbiosciences.com/jp/instruments/software/facsuite/index.jsp> [searched on Aug. 20, 2018] (Non Patent Literature 1) and the Internet <https://ls.beckmancoulter-co.jp/products/flow-cytometers/> [searched on Aug. 20, 2018] (Non Patent Literature 2)).

In a specimen analysis system using a flow cytometry as described above, it is inconvenient for a user that the format of a report including desired measurement data cannot be changed.

In addition, the format of a report including measurement data is predetermined not only by each company that provides a specimen analysis system but also by each facility at which a clinical test using a flow cytometry is performed. The format is prohibited from being freely changed. Currently in such a case, a laboratory technician or the like prints reports and further produces a paper report by collecting and collaging a plurality of parts on which desired measurement data are presented. Moreover, since the format of a report is different between companies and facilities, an experienced and skilled laboratory technician capable of sufficiently understanding the detailed information of a reagent and the detailed data of a measurement result is needed to obtain a report on which desired measurement data are presented.

Thus, one or more aspects may provide a specimen analysis system and a specimen analysis method that significantly improve user convenience and do not need special technical experts.

SUMMARY

A specimen analysis system according to one or more aspect may include: a measurement data acquisition unit that acquires measurement data of particles obtained from a flow cytometer measuring the particles contained in a measurement specimen prepared by adding a reagent to a sample; an output mode information acquisition unit that acquires output mode information indicating an output form of the measurement data; and an output unit configured to output the measurement data in the output form in accordance with the output mode information.

A specimen analysis method, according to one or more aspect, which is executed by a computer, may include: acquiring measurement data of particles obtained from a flow cytometer measuring the particles contained in a measurement specimen prepared by adding a reagent to a sample; acquiring output mode information indicating an output form of the measurement data; and outputting the measurement data in the output form in accordance with the output mode information.

A specimen analysis system according to one or more aspects may include: a measuring unit configured to acquire measurement data of particles by measuring, using a flow cytometry, the particles contained in a measurement specimen prepared by adding a reagent to a sample; a reagent information acquisition unit that acquires reagent information whether the reagent comprises an in-vitro diagnostics reagent for use in in-vitro diagnosis; and an output unit configured to output the measurement data based on the reagent information.

A specimen analysis method according to one or more aspects may include: acquiring measurement data of particles by measuring, using a flow cytometry, the particles contained in a measurement specimen prepared by adding a reagent to a sample; acquiring reagent information whether the reagent comprises an in-vitro diagnostics reagent for use in in-vitro diagnosis; and outputting the measurement data based on the reagent information.

BRIEF DESCRIPTION OF DRAWINGS

FIG. 4 is a diagram illustrating exemplary information included in a measurement condition according to one or more embodiments, in which FSC represents forward scattered light, SSC represents side scattered light, FL1, FL2, FL3, and FL4 represent four kinds of fluorescence having different peak wavelengths, and ch represents channel;

DETAILED DESCRIPTION

Figure 1:
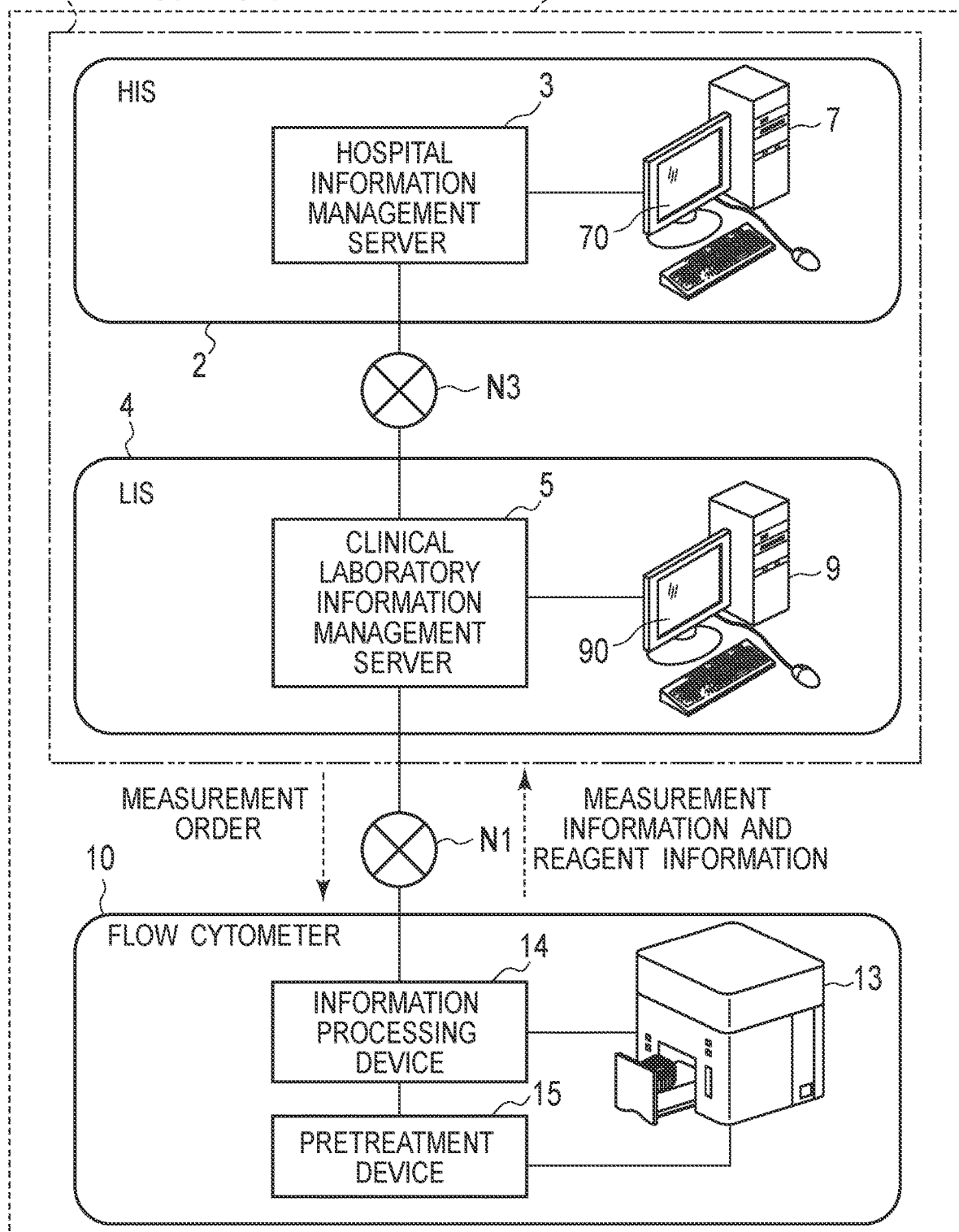
FIG. 1 is a diagram illustrating an exemplary schematic diagram of a specimen analysis system according to one or more embodiments.

A specimen analysis system (1) according to one or more aspects is a specimen analysis system using a flow cytometry, the system including: a measurement data acquisition unit (633) that acquires measurement data of particles obtained from a flow cytometer measuring the particles contained in a measurement specimen prepared by adding a reagent to a sample; an output mode information acquisition unit (635) that acquires output mode information indicating an output form of the measurement data; and an output unit (62, 70, 90) that outputs the measurement data in the output form in accordance with the output mode information.

With the above-described specimen analysis system (1), measurement data of particles is output in an output form in accordance with output mode information indicating the output form of the measurement data. Thus, it is possible to provide a report in a format desired by a user and significantly improve convenience for the user. In addition, a report can be automatically produced in accordance with the output mode information, and thus it is not needed to educate and train an experienced and skilled technical expert to perform report production work and it is not needed to employ an experienced and skilled technical expert. Accordingly, it is possible to establish a specimen analysis system for which no special technical expert is needed.

In the above-described specimen analysis system (1), the output mode information may include information indicating whether the measurement data includes only a test value of the particles contained in the measurement specimen or whether the measurement data includes, in addition to the test value, at least one of particle data including optical information of the particles contained in the measurement specimen and data on a particle distribution diagram of the particles generated based on the particle data, and the output unit may output the measurement data based on the information in a manner that enables identifying, distinguishing, or recognizing whether the measurement data includes only the test value or whether the measurement data includes, in addition to the test value, at least one of particle data including optical information of the particles contained in the measurement specimen and data on a particle distribution diagram of the particles generated based on the particle data.

With the above-described specimen analysis system (1), the measurement data is output based on the acquired information in a manner that enables identifying, distinguishing, or recognizing whether the measurement data includes only the test value or whether the measurement data includes, in addition to the test value, at least one of particle data including optical information of the particles contained in the measurement specimen and data on a particle distribution diagram of the particles generated based on the particle data. With this configuration, it is possible to prevent a doctor or the like from performing false diagnosis and reporting a false analysis result, and thus it is possible to provide a report in a format in accordance with the content of measurement data and significantly improve convenience for the user. In addition, it is possible to automatically produce a report in accordance with the content of measurement data, and thus it is not needed to educate and train an experienced and skilled technical expert to perform report production work and it is not needed to employ an experienced and skilled technical expert. Accordingly, it is possible to establish a specimen analysis system for which no special technical expert is needed.

In the above-described specimen analysis system (1), the output mode information may include reagent information that enables identifying, distinguishing, or recognizing whether the reagent is an in-vitro diagnostics reagent for use in in-vitro diagnosis, and the output unit may output the measurement data based on the reagent information in a manner that enables identifying, distinguishing, or recognizing whether the measurement data is measurement data of the particles contained in the measurement specimen prepared through addition of the in-vitro diagnostics reagent.

With the above-described specimen analysis system (1), the measurement data is output based on the reagent information in a manner that enables identifying, distinguishing, or recognizing whether the measurement data is measurement data of the particles contained in the measurement specimen prepared through addition of the in-vitro diagnostics reagent for use in in-vitro diagnosis. With this configuration, it is possible to prevent a doctor or the like from performing false diagnosis and reporting a false analysis result, and thus it is possible to provide a report in a format in accordance with the reagent information and significantly improve convenience for the user. In addition, it is possible to automatically produce a report in accordance with the reagent information, and thus it is not needed to educate and train an experienced and skilled technical expert to perform report production work and it is not needed to employ an experienced and skilled technical expert. Accordingly, it is possible to establish a specimen analysis system for which no special technical expert is needed. In addition, it is possible to produce a report in accordance with the reagent information and thus appropriately output the measurement data when an optional reagent is selected by the user.

The above-described specimen analysis system (1) may further include a storage unit (83) that stores identification information of the sample and reagent information of the reagent added to the sample in association with each other, and, when outputting the measurement data for each sample, the output unit (62, 70, 90) may output the measurement data based on the identification information and the reagent information in a manner that enables identifying, distinguishing, or recognizing whether the reagent added to the sample is the in-vitro diagnostics reagent.

With the above-described specimen analysis system (1), when the measurement data is output for each sample, the measurement data is output in a manner that enables identifying, distinguishing, or recognizing whether the reagent added to the sample is the in-vitro diagnostics reagent. With this configuration, when the measurement data is output for each sample, it is possible to easily determine whether the reagent added to each of a plurality of samples is the in-vitro diagnostics reagent.

The above-described specimen analysis system (1) may further include a reading unit (60) that reads a code attached to a reagent container in which the reagent is stored, and the output mode information acquisition unit (635) may acquire reagent information of the reagent, which is included in the read code.

With the above-described specimen analysis system (1), a code attached to a reagent container in which the reagent is stored is read, and reagent information of the reagent, which is included in the read code is acquired. Thus, it is possible to reliably and easily acquire the reagent information.

In the above-described specimen analysis system (1), the output unit (62, 70, 90) may output, on an identical or same screen or an identical or same sheet, measurement data of the particles contained in the measurement specimen prepared through addition of the in-vitro diagnostics reagent and measurement data of the particles contained in the measurement specimen prepared through addition of a reagent other than the in-vitro diagnostics reagent.

With the above-described specimen analysis system (1), the output unit outputs, on an identical or same screen or an identical or same sheet, measurement data based on the in-vitro diagnostics reagent and measurement data based on the reagent other than the in-vitro diagnostics reagent. With this configuration, it is not needed to switch screens to check the measurement data based on the in-vitro diagnostics reagent and the measurement data based on a reagent other than the in-vitro diagnostics reagent, and thus it is possible to improve convenience for the user.

In the above-described specimen analysis system (1), the output unit (62, 70, 90) may output, in different regions on an identical or same screen or an identical or same sheet, measurement data of the particles contained in the measurement specimen prepared through addition of the in-vitro diagnostics reagent and measurement data of the particles contained in the measurement specimen prepared through addition of a reagent other than the in-vitro diagnostics reagent.

With the above-described specimen analysis system (1), the output unit outputs, in different regions on an identical or same screen or an identical or same sheet, measurement data based on the in-vitro diagnostics reagent and measurement data based on a reagent other than the in-vitro diagnostics reagent. With this configuration, it is possible to easily identify the measurement data based on the in-vitro diagnostics reagent and the measurement data based on a reagent other than the in-vitro diagnostics reagent.

In the above-described specimen analysis system (1), the output unit (62, 70, 90) may display, in a switching manner, a screen on which measurement data of the particles contained in the measurement specimen prepared through addition of the in-vitro diagnostics reagent is output and a screen on which measurement data of the particles contained in the measurement specimen prepared through addition of a reagent other than the in-vitro diagnostics reagent is output.

With the above-described specimen analysis system (1), the screen on which measurement data based on the in-vitro diagnostics reagent is output and the screen on which measurement data based on a reagent other than the in-vitro diagnostics reagent is output are displayed in a switching manner. With this configuration, it is possible to reliably identify the measurement data based on the in-vitro diagnostics reagent and the measurement data based on a reagent other than the in-vitro diagnostics reagent.

In the above-described specimen analysis system (1), the output unit (62, 70, 90) may output, in different output forms, measurement data of the particles contained in the measurement specimen prepared through addition of the in-vitro diagnostics reagent and measurement data of the particles contained in the measurement specimen prepared through addition of a reagent other than the in-vitro diagnostics reagent.

With the above-described specimen analysis system (1), measurement data based on the in-vitro diagnostics reagent and measurement data based on a reagent other than the in-vitro diagnostics reagent are output in different output forms. With this configuration, it is possible to easily identify, without distinguishing output regions, the measurement data based on the in-vitro diagnostics reagent and the measurement data based on a reagent other than the in-vitro diagnostics reagent.

In the above-described specimen analysis system (1), the storage unit (83) may further store facility identification information to identify a facility at which a clinical test using the flow cytometry is performed, and the output unit (62, 70, 90) may output the measurement data based on the facility identification information in a manner that enables identifying, distinguishing, or recognizing whether the measurement data is measurement data of the particles contained in the measurement specimen prepared through addition of the in-vitro diagnostics reagent.

With the above-described specimen analysis system (1), the output unit outputs the measurement data based on the facility identification information in a manner that enables identifying, distinguishing, or recognizing whether the measurement data is measurement data of the particles contained in the measurement specimen prepared through addition of the in-vitro diagnostics reagent. With this configuration, it is possible to easily determine whether measurement data obtained at a particular facility that satisfies a certain condition is measurement data based on the in-vitro diagnostics reagent.

In the above-described specimen analysis system (1), the reagent information may include reagent information that enables identifying, distinguishing, or recognizing whether the reagent is the in-vitro diagnostics reagent or an analyte specific reagent (ASR).

With the above-described specimen analysis system (1), the reagent information includes reagent information that enables identifying, distinguishing, or recognizing whether the reagent is the in-vitro diagnostics reagent or an analyte specific reagent (ASR). With this configuration, it is possible to identify whether the reagent added to the sample is the in-vitro diagnostics reagent or the ASR.

In the above-described specimen analysis system (1), the output unit (62, 70, 90) may output the measurement data based on the reagent information in a manner that enables identifying, distinguishing, or recognizing whether the measurement data is measurement data of the particles contained in the measurement specimen prepared through addition of the ASR.

With the above-described specimen analysis system (1), the output unit outputs the measurement data based on the reagent information in a manner that enables identifying, distinguishing, or recognizing whether the measurement data is measurement data of the particles contained in the measurement specimen prepared through addition of the ASR. With this configuration, when the measurement data is output, it is possible to easily determine whether the measurement data is measurement data based on the ASR.

The above-described specimen analysis system (1) may further include a pretreatment device (15) that prepares the measurement specimen through addition of the reagent to the sample.

The above-described specimen analysis system (1) includes a pretreatment device that prepares the measurement specimen through addition of the reagent to the sample. With this configuration, the measurement specimen to be measured can be appropriately prepared at a stage before main measurement treatment for acquisition of the measurement data.

In the above-described specimen analysis system (1), the measurement data acquisition unit (633) may acquire measurement data obtained from a measurement device other than the flow cytometer, and the output unit (62, 70, 90) may output the measurement data obtained from the measurement device.

With the above-described specimen analysis system (1), the measurement data acquisition unit acquires measurement data obtained from a measurement device other than the flow cytometer, and the output unit outputs the measurement data obtained from the measurement device. With this configuration, it is possible to collectively output not only measurement data obtained from the flow cytometer but also measurement data obtained from a measurement device other than the flow cytometer.

In the above-described specimen analysis system (1), the output unit (62, 70, 90) may output the measurement data obtained from the measurement device, as measurement data other than measurement data of the particles contained in the measurement specimen prepared through addition of the in-vitro diagnostics reagent.

With the above-described specimen analysis system (1), the output unit outputs measurement data obtained from a measurement device other than the flow cytometry, as measurement data other than measurement data of the particles contained in the measurement specimen prepared through addition of the in-vitro diagnostics reagent. With this configuration, when the measurement data obtained from the measurement device other than the flow cytometry is output, it is possible to easily identify the measurement data.

In the above-described specimen analysis system (1), the measurement data obtained from the measurement device may include measurement data obtained through at least one of a hematology test, a blood smear test, an image diagnosis, a blood coagulation test, an immunity test, a biochemical test, a urine test, and a gene test.

With the above-described specimen analysis system (1), measurement data obtained from a measurement device other than the flow cytometry includes measurement data obtained through at least one of a hematology test, a blood smear test, an image diagnosis, a blood coagulation test, an immunity test, a biochemical test, a urine test, and a gene test. With this configuration, measurement data obtained by various test methods can be acquired from the measurement device other than the flow cytometry.

In the above-described specimen analysis system (1), the measurement data obtained from the measurement device may be data acquired from any one of a hospital information system (2) that supports hospital operations, a clinical laboratory information system (4) that supports clinical test operations, and a test information management system.

With the above-described specimen analysis system (1), measurement data obtained from a measurement device other than the flow cytometry is data acquired from any one of a hospital information system, a clinical laboratory information system, and a test information management system. With this configuration, measurement data can be acquired from another system other than the flow cytometry.

In the above-described specimen analysis system (1), the output unit (62, 70, 90) may output a result of accuracy control of the flow cytometer as data other than measurement data of the particles contained in the measurement specimen prepared through addition of the in-vitro diagnostics reagent.

With the above-described specimen analysis system (1), the output unit may further output the result of accuracy control of the flow cytometer as data other than measurement data based on the in-vitro diagnostics reagent. With this configuration, the result of accuracy control of the flow cytometer can be included in a report, which assures the reliability of measurement data.

A specimen analysis method according to one or more aspects is a specimen analysis method using the flow cytometry, which is executed by a computer, the method including: acquiring measurement data of particles obtained from a flow cytometer measuring the particles contained in a measurement specimen prepared by adding a reagent to a sample; acquiring output mode information indicating an output form of the measurement data; and outputting the measurement data in the output form in accordance with the output mode information.

With the above-described specimen analysis method, measurement data of particles is output in an output form in accordance with output mode information indicating the output form of the measurement data. Thus, it is possible to provide a report in a format desired by a user and significantly improve convenience for the user. In addition, a report can be automatically produced in accordance with the output mode information, and thus it is not needed to educate and train an experienced and skilled technical expert to perform report production work and it is not needed to employ an experienced and skilled technical expert. Accordingly, it is possible to establish a specimen analysis system for which no special technical expert is needed.

A specimen analysis system according to one or more aspects is a specimen analysis system, including: a measuring unit configured to acquire measurement data of particles by measuring, using a flow cytometry, the particles contained in a measurement specimen prepared by adding a reagent to a sample; a reagent information acquisition unit that acquires reagent information whether the reagent comprises an in-vitro diagnostics reagent for use in in-vitro diagnosis; and an output unit configured to output the measurement data based on the reagent information.

A specimen analysis method according to one or more aspects is a specimen analysis method, including: acquiring measurement data of particles by measuring, using a flow cytometry, the particles contained in a measurement specimen prepared by adding a reagent to a sample; acquiring reagent information whether the reagent comprises an in-vitro diagnostics reagent for use in in-vitro diagnosis; and outputting the measurement data based on the reagent information.

The present disclosure provides a specimen analysis system and a specimen analysis method that significantly improve convenience for a user and for which no special technical expert is needed.

The following describes embodiments with the accompanying drawings. In the drawings, components denoted by an identical reference sign have identical or similar configurations.

[Specimen Analysis System]

FIG. 1 is a diagram illustrating an exemplary schematic diagram of a network configuration with a specimen analysis system according to one or more embodiments. As illustrated in FIG. 1, as an example, this specimen analysis system 1 includes a flow cytometer 10 and an electronic medical record system 50. The flow cytometer 10 is a measurement device used to perform flow cytometry as a method of optically detecting the size, the structure, the fluorescence intensity, and the like of each of particles dispersed in liquid and measuring the number and distribution of the particles based on information thus detected. For example, the flow cytometer 10 has a function of detecting individual particles by a sheath flow scheme.

As illustrated in FIG. 1, the flow cytometer 10 is installed at, for example, a hospital or a test facility and includes, as an example, a flow cytometer body 13, an information processing device 14 connected with the flow cytometer body 13, and a pretreatment device 15 that prepares a measurement specimen through addition of a reagent to a sample. Specific configurations of the flow cytometer body 13 and the information processing device 14 will be described later.

The electronic medical record system 50 collects information on a test result (measurement data) obtained from the flow cytometer 10 as well as various kinds of information such as the full name, age, ID, therapeutic medicine kind and dosage amount, medical examination details, medical treatment details, treatment details, disease name, various medical test orders, and an event such as an operation of a patient, and generates and manages an electronic medical record (report). The report includes a medical record and a test result report on paper in addition to an electronic medical record. The report may be managed at the flow cytometer 10.

The flow cytometer 10 is connected with the electronic medical record system 50 through a communication network N1. The communication network N1 is a communication medium such as the Internet, a virtual private network (VPN), a wide area communication network (WAN), or a public switched telephone network (PSTN) but not limited thereto, and may be any network through which communication can be performed between the flow cytometer 10 and the electronic medical record system 50.

As illustrated in FIG. 1, as an example, the electronic medical record system 50 includes a hospital information system (HIS) 2 that supports hospital operations, and a clinical laboratory information system (LIS) 4 that supports clinical test operations. The electronic medical record system 50 may include another system such as a test information management system that manages test information.

As an example, the HIS 2 includes a hospital information management server 3 having, for example, a function of electrically managing an instruction (order) for a test, prescription, or the like performed by a doctor or a nurse, a medical accounting function, and a function of generating and managing an electronic medical record, and a doctor terminal device 7 including an output unit 70 (output unit) that outputs, for example, an electronic medical record or another report.

The LIS 4 is an information system that handles general test operations performed by a laboratory technician or the like at a medical facility such as a hospital, and includes a clinical laboratory information management server 5 having, for example, a function of accepting a test, a function of reporting a test result, and a function of supporting a test flow such as data management, and a laboratory technician terminal device 9 including an output unit 90 (output unit) that outputs, for example, a screen on which a laboratory technician browses test details. The LIS 4 may have a function of generating and managing an electronic medical record or a report.

As described above, a measurement order is transmitted from the electronic medical record system 50 to a flow cytometer 10, but may be transmitted from the HIS 2 through the LIS 4 based on, for example, an instruction from a doctor. Alternatively, the measurement order may be transmitted from the LIS 4 to the flow cytometer 10 based on, for example, an instruction from a laboratory technician.

As illustrated in FIG. 1, the HIS 2 and the LIS 4 are connected with each other through a communication network N3. The communication network N3 is a communication medium such as the Internet, a virtual private network (VPN), a wide area communication network (WAN), or a public switched telephone network (PSTN) but not limited thereto, and may be any network through which communication can be performed between the HIS 2 and the LIS 4.

The number of flow cytometers 10 connected with the electronic medical record system 50 is not limited, but a plurality of flow cytometers 10 may be connected with the electronic medical record system 50. In addition, the numbers of HISs 2 and LISs 4 included in the electronic medical record system 50 are not particularly limited.

The following describes the overview of one or more embodiments. As illustrated in FIG. 1, the flow cytometer 10 acquires a measurement order including one or a plurality of measurement items from the electronic medical record system 50, and adds a reagent to a sample in accordance with the one or plurality of measurement items included in the measurement order. As pretreatment, the flow cytometer 10 measures particles contained in a measurement specimen prepared through addition of the reagent to acquire measurement data of the particles. The flow cytometer 10 acquires output mode information indicating the output form of the measurement data, and transmits the measurement data and the output mode information to the electronic medical record system 50. The output unit 70 or 90 included in the electronic medical record system outputs the measurement data in the output form in accordance with the output mode information. As described later, the measurement data may be output on a display unit 62 of the flow cytometer illustrated in FIG. 5.

According to the specimen analysis system 1 in one or more embodiments, the measurement data of particles can be output in an output form in accordance with the output mode information indicating the output form of the measurement data. Thus, it is possible to provide a report in a format desired by a user and significantly improve convenience for the user. In addition, a report can be automatically produced in accordance with the output mode information, and thus it is not needed to educate and train an experienced and skilled technical expert to perform report production work and it is not needed to employ an experienced and skilled technical expert. Accordingly, it is possible to establish a specimen analysis system for which no special technical expert is needed.

The measurement data is data on particles when the particles are measured, and includes, for example, particle data including optical information of the particles. The measurement data may include data on a particle distribution diagram (at least one of a dot plot, a scattergram, and a histogram) of the particles generated based on the particle data. In addition, the measurement data may include a test value (for example, information indicating the number of blood cells such as lymphocytes, monocytes, and granulocytes) of the particles. The optical information is information included in one or a plurality of light wavelength spectra emitted from the particles. Each light wavelength spectrum includes an individual light wavelength and an individual light wavelength region included in the light wavelength spectrum, and the strength of each light wavelength or each light wavelength region. The individual light wavelength and the individual wavelength region can be specified based on which of one or a plurality of light receiving elements (for example, refer to a photodiode 100A, an APD 100B, and PMTs 100C to 100F in FIG. 5) to be described later has received the light. The strength of each light wavelength or light wavelength region can be specified based on an electric signal output from a light receiving element having received the light. As an example, the optical information includes forward scattered light information indicating the size of a cell (particle), side scattered light information indicating the internal structure of the cell, and fluorescence information indicating development of protein, gene, or the like in the cell. When having acquired the measurement data of the particles from the flow cytometer 10, the electronic medical record system 50 converts the acquired measurement data into data such as a particle distribution diagram, which can be output, and generates and outputs an electronic medical record or any other report including the particle distribution diagram. The measurement data may further include particle number information on the number of particles. The particle number information includes, for example, the number of blood cells such as lymphocytes, monocytes, and granulocytes.

Each measurement item is information referred to at pretreatment of a sample and measurement of particles, and is, for example, the kind of particles, and the kind of material existing at the particles. Examples of the measurement items include the kind of cell, the kind of protein, the kind of sugar chain, the kind of lipid, the kind of glycoprotein, the kind of glycolipid, the kind of lipoprotein, and the kind of nucleic acid. As described later, the measurement order may include a measurement condition of measurement at the flow cytometer 10.

The output mode information may also include various kinds of information. For example, the output mode information includes information indicating whether the measurement data includes only the test value of particles contained in the measurement specimen or whether the measurement data includes, in addition to the test value, at least one of the particle data including the optical information of the particles contained in the measurement specimen and the data on the particle distribution diagram of the particles generated based on the particle data. When the measurement data includes only the test value, the specimen analysis system 1 may output, from the output unit (62, 70, 90), the measurement data in a manner that enables identifying, distinguishing, or recognizing that the measurement data is measurement data including only the test value. When the measurement data includes, in addition to the test value, the particle data including the optical information of the particles contained in the measurement specimen, the specimen analysis system 1 may output, from the output unit (62, 70, 90), the measurement data in a manner that enables identifying, distinguishing, or recognizing that the measurement data is measurement data including the particle data in addition to the test value. When the measurement data includes, in addition to the test value, data on the particle distribution diagram of the particles generated based on the particle data, the specimen analysis system 1 may output, from the output unit (62, 70, 90), the measurement data in a manner that enables identifying, distinguishing, or recognizing that the measurement data is measurement data including the data on the particle distribution diagram of the particles in addition to the test value. When the measurement data includes, in addition to the test value, both of the particle data and the data on the particle distribution diagram of the particles, the specimen analysis system 1 may output, from the output unit (62, 70, 90), the measurement data in a manner that enables identifying, distinguishing, or recognizing that the measurement data is measurement data including, in addition to the test value, both of the particle data and the data on the particle distribution diagram of the particles.

The flow cytometer 10 also acquires, as the output mode information, reagent information that enables identifying, distinguishing, or recognizing whether a reagent used in pretreatment is an in-vitro diagnostics reagent for use in in-vitro diagnosis. The flow cytometer 10 transmits the measurement data and the reagent information thus acquired to the electronic medical record system 50. The output unit 70 or the output unit 90 included in the electronic medical record system 50 outputs the measurement data based on the acquired reagent information in a manner that enables identifying, distinguishing, or recognizing whether the measurement data is measurement data of the particles contained in the measurement specimen prepared through addition of the in-vitro diagnostics reagent. As described later, the measurement data may be output on the display unit 62 of the flow cytometer illustrated in FIG. 5.

The reagent information includes information that enables identifying, distinguishing, or recognizing the reagent, more specifically, information indicating whether the reagent is an in-vitro diagnostics reagent (IVD reagent) or a reagent for other usage, such as a research use only reagent (RUO reagent). The reagent information may further include reagent information that enables identifying, distinguishing, or recognizing whether the regent is an analyte specific reagent (ASR). The reagent is not limited to the above-described three reagents, but may include another reagent. The reagent information includes information on, for example, a reagent name, a reagent ID, a reagent standard, a dose, and a price.

The following describes difference between a method of outputting the measurement data based on the reagent information in one or more embodiments and an outputting method in a specimen analysis system as disclosed in Non-Patent Literatures 1 and 2 described above. First, the format of a report including clinical test use measurement data is prohibited from being freely changed in the conventional specimen analysis system, thereby preventing a doctor or the like from performing false diagnosis and reporting a false analysis result. However, such prohibition from changing the format of a report is inconvenient for the user.

The conventional specimen analysis system does not enable provision of a report including research use measurement data and clinical test use measurement data on an identical or same screen or an identical or same sheet. This is to prevent a doctor from performing false diagnosis and reporting a false analysis result due to mixture of the research use measurement data and the clinical test use measurement data on an identical or same screen or an identical or same sheet. However, such prevention is inconvenient for a user who desires to simultaneously browse the research use measurement data and the clinical test use measurement data on an identical or same screen or an identical or same sheet.

In addition, the format of a report including measurement data is predetermined not only for each company that provides a conventional specimen analysis system but also for each facility at which a clinical test using a flow cytometry is performed, and free change of the format is prohibited. Currently in such a case, a laboratory technician or the like prints the report and further produces a paper report by collecting and collaging a plurality of parts on which desired measurement data are presented. Moreover, since the format of a report is different between companies and facilities, an experienced and skilled laboratory technician capable of sufficiently understanding the detailed information of a reagent and the detailed data of a measurement result is needed to obtain a report on which desired measurement data are presented.

In addition, it is impossible to produce an appropriate report without using a reagent recommended for each company and each facility. The format of a report for a company supports only a case in which a particular reagent recommended by the company is used, but does not support a case in which a reagent other than the particular reagent is used. In this manner, it is impossible to appropriately output a desired report, depending on a reagent selected by a user.

However, the method of outputting measurement data based on the reagent information in one or more embodiments can provide a specimen analysis system that significantly improves convenience for a user, for which no special technical expert is needed, and that can appropriately output the measurement data when an optional reagent is selected by the user.

Figure 2:
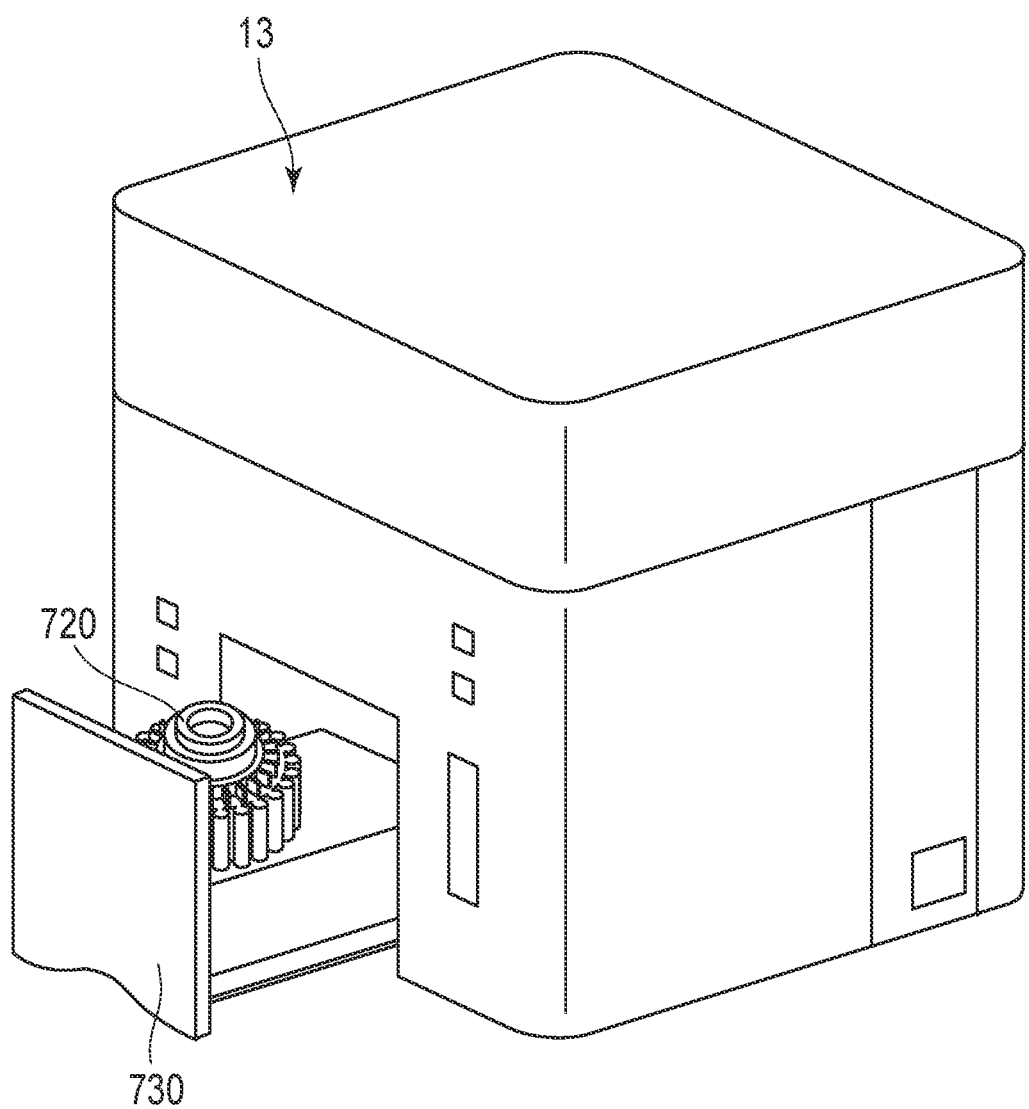
FIG. 2 is a diagram illustrating an exemplary exterior diagram of a flow cytometer according to one or more embodiments.

FIG. 2 is a diagram illustrating an exemplary exterior diagram of the flow cytometer according to one or more embodiments. As illustrated in FIG. 2, as an example, the flow cytometer body 13 includes a housing unit 730 housing a specimen container 720 in which a measurement specimen prepared through pretreatment is housed, and an aspiration unit (not illustrated) that can elevate and horizontally move. For example, as illustrated in FIG. 2, the specimen container 720 is positioned inside the flow cytometer body 13 by placing the specimen container 720 in the housing unit 730 and moving the housing unit 730 into the flow cytometer body 13. Then, measurement of the measurement specimen in the specimen container 720 is instructed to the flow cytometer. Accordingly, the aspiration unit aspirates the measurement specimen from the specimen container 720 positioned inside the flow cytometer body 13.

[Optical System of Flow Cytometer]

Figure 3:
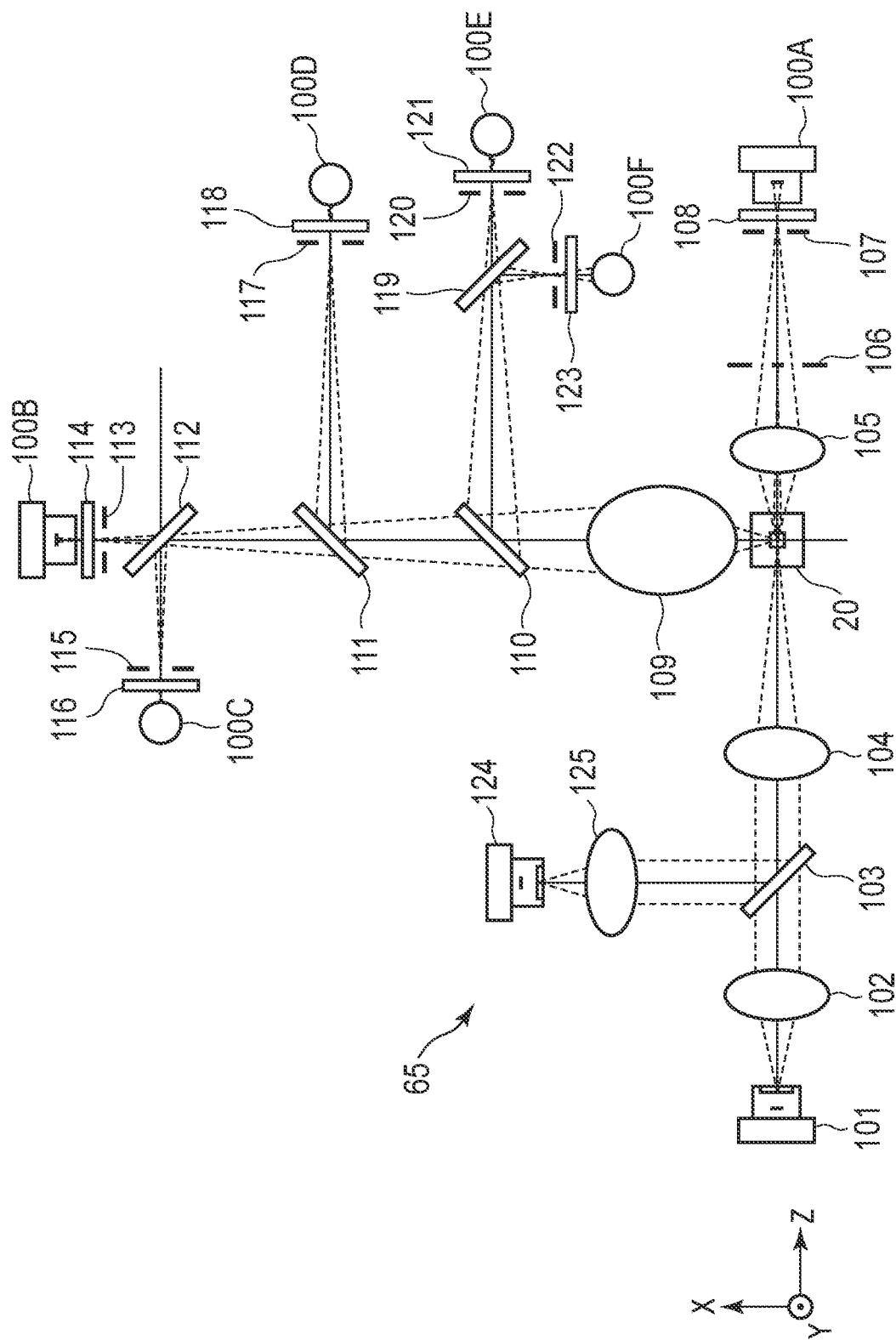
FIG. 3 is a diagram illustrating an exemplary optical system of a flow cytometer according to one or more embodiments.

FIG. 3 is a diagram illustrating an exemplary optical system of the flow cytometer according to one or more embodiments. The flow cytometer 10 includes a flow cell 20 through which particle-containing liquid containing particles in a sample passes, light sources 101 and 124 that emit light onto the particles passing through the flow cell 20, and light receiving elements 100A to 100F that detect the optical information of particle-attributable light and output a detection signal converted into an electric signal.

The particles preferably emit one or a plurality of kinds of light when irradiated with predetermined light. Light emitted from the particles when irradiated with the predetermined light is collectively referred to as particle-attributable light. The particle-attributable light includes scattered light, emitted light, and the like. The particle-attributable light may be light having any wavelength, but is preferably light having a peak wavelength in the range of 350 nm to 850 nm. More specifically, the particle-attributable light is preferably fluorescence. The particle-attributable light may be emitted light, such as autofluorescence, attributable to material contained in the particles. Alternatively, the particles may be labeled with a light emission material such as fluorescent substance, and light emitted from the light emission material may be detected as the particle-attributable light. The peak wavelength of the particle-attributable light is preferably different between measurement items.

The particle-containing liquid includes particle suspension aspirated from the specimen into the flow cytometer, and contains diluent as necessary.

The following specifically describes examples in which the particle-attributable light is scattered light and fluorescence.

Light emitted from the light source 101 is incident on the flow cell 20 through a collimate lens 102, a dichroic mirror 103, and a condenser lens 104. Forward scattered light of the particle-attributable light passing through the flow cell 20 is condensed through a condenser lens 105 and incident on the light receiving element 100A through a beam stopper 106, a pin-hole plate 107, and a band-pass filter 108.

Side scattered light and side fluorescence and the particle-attributable light passing through the flow cell 20 is condensed through a condenser lens 109. The side scattered light is incident on the light receiving element 1008 through dichroic mirrors 110, 111, and 112, a pin-hole plate 103, and a band-pass filter 114. The side fluorescence having a wavelength of 520 nm to 542 nm inclusive transmits through the dichroic mirrors 110 and 111 and is reflected by the dichroic mirror 112 and incident on the light receiving element 100C through a pin-hole plate 115 and a band-pass filter 116. The side fluorescence having a wavelength of 570 nm to 620 nm inclusive transmits through the dichroic mirror 110 and is reflected by the dichroic mirror 111 and incident on the light receiving element 100D through a pin-hole plate 117 and a band-pass filter 118. The side fluorescence having a wavelength of 670 nm to 800 nm inclusive is reflected by the dichroic mirror 110, transmits through a dichroic mirror 119, and is incident on the light receiving element 100E through a pin-hole plate 120 and a band-pass filter 121.

Light emitted from a light source 124 is incident on the flow cell 20 through a collimate lens 125, the dichroic mirror 103, and the condenser lens 104. Side fluorescence of the particle-attributable light passing through the flow cell 20 is condensed through the condenser lens 109. The side fluorescence having a wavelength of 662.5 nm to 687.5 nm inclusive is reflected by the dichroic mirror 110 and the dichroic mirror 119 and then incident on the light receiving element 100F through a pin-hole plate 122 and a band-pass filter 123.

In one or more embodiments, for example, the light source 101 is a laser diode having a wavelength of 488 nm, and the light source 124 is a laser diode having a wavelength of 642 nm. The flow cell 20 is a sheath flow cell. The light receiving element 100A, which receives forward scattered light, is a photodiode, the light receiving element 100B, which receives side scattered light, is an avalanche photodiode (APD), and the light receiving elements 100C to 100F, which receive side fluorescence, are photomultiplier tubes (PMTs). In one or more embodiments, the flow cytometer 10 includes the six light receiving elements 100A to 100F. The four light receiving elements 100C to 100F detect the optical information of four respective kinds of light having different peak wavelengths attributable to pigments coupled with particles in the specimen, but are not limited thereto. For example, when the flow cytometer 10 includes three or more light receiving elements, at least two of the three or more light receiving elements may detect the optical information of respective kinds of light attributable to at least two pigments having different peak wavelengths. For example, in a HIV test, when four kinds of labeling antibody pigments coupled with CD4, CD45, CD8, and CD3, respectively, on a cell surface are used, four kinds of fluorescence having four peak wavelengths attributable to the respective labeling antibody pigments in response to markers existing on the cell surface are generated from the measurement specimen and can be detected by the four light receiving elements 100C to 100F.

The number of light sources may be one or equal to or larger than two. Each light source is selected in accordance with the wavelength region of light attributable to a pigment coupled with a particle. When the number of light sources is equal to or larger than two, these light sources preferably emit light having different peak wavelengths. The number of light sources is preferably equal to or larger than two because a plurality of kinds of fluorescence can be accurately separated and detected as compared to a case in which the number of light sources is one. For example, when one light source is used in a HIV test, FITC is used as a labeling antibody pigment for CD4 and PE5 is used as a labeling antibody pigment for CD8 in some cases. Since the peak wavelength of fluorescence from the FITC and the peak wavelength of fluorescence from the PE are close to each other, the overlapping part of the wavelength regions thereof tends to be large. However, when two light sources are used, a plurality of kinds of fluorescence can be separated and detected by shifting the timings of light emission from the light sources. In addition, the overlapping part of the wavelength regions of a plurality of kinds of fluorescence can be reduced by using a pigment suitable for the peak wavelength of light from each light source. For example, in place of PE, APC can be used as the labeling antibody pigment for CD8. The numbers of photodiodes, dichroic mirrors, and band-pass filters are can be changed in accordance with the number of peak wavelengths of the particle-attributable light. In addition, the kinds of photodiode, dichroic mirror, and band-pass filter can be selected in accordance with the peak wavelength or wavelength region of the particle-attributable light, and the strength thereof.

Figure 5:
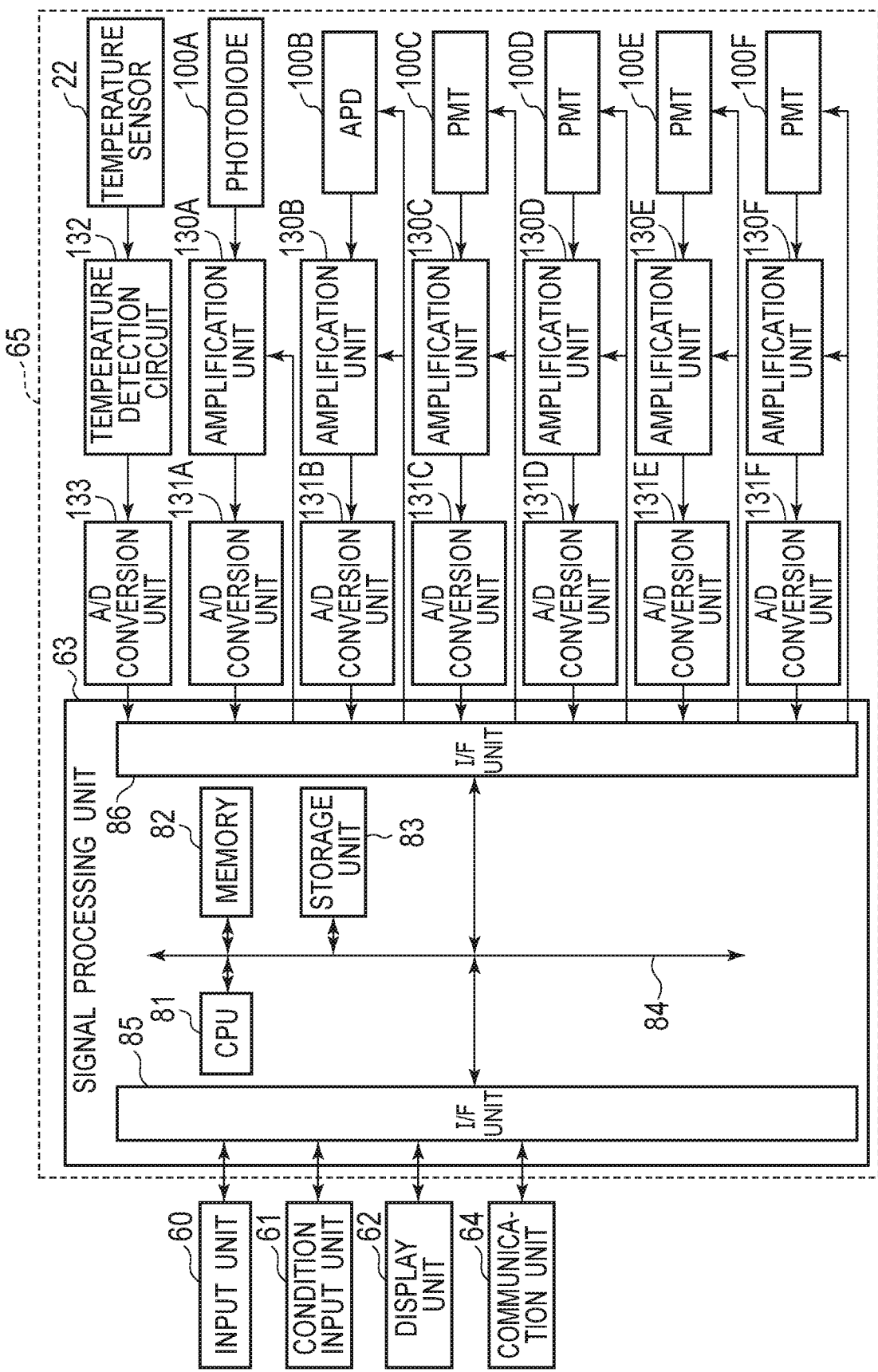
FIG. 5 is a diagram illustrating an exemplary information processing system of a flow cytometer according to one or more embodiments.

As illustrated in FIG. 5 to be described later, the detection signals output from the respective light receiving elements 100A to 100F are amplified by amplification units 130A to 130F, A/D converted by A/D conversion units 131A to 131F, and input to a signal processing unit 63. Specifically, the amplification units 130A and 130B connected with the light receiving element 100A as a photodiode and the light receiving element 100B as an APD are known amplification circuits such as operational amplifiers, and adjust the output voltages of the light receiving elements 100A and 100B, which are input thereto, by adjusting the degree of amplification at each amplification circuit. In addition, the values of voltage applied to the light receiving elements 100C to 100F as PMTs are changed to adjust the output voltages of the PMTs. Hereinafter, adjustment of the detection sensitivities of the light receiving elements 100A to 100F is adjustment of the degree of amplification of amplification circuits at the light receiving elements 100A and 100B, and adjustment of voltages applied to the light receiving elements 100C to 100F at the light receiving elements 100C to 100F. The detection signals output from the light receiving elements 100A and 100B are amplified by adjusting the degree of amplification of amplification circuits at the light receiving elements, and the detection signals output from the light receiving elements 100C to 100F are adjusted by adjusting the voltages applied to the light receiving elements 100C to 100F. Amplification includes a case in which the ratio of an output signal relative to an input signal is equal to or larger than one and a case in which the ratio is smaller than one. The amplification units 130C to 130F connected with the light receiving elements 100C to 100F may further include known amplification circuits, and adjustment of the detection sensitivities of the light receiving elements 100C to 100F may include adjustment of the output voltages of the light receiving elements 100C to 100F by these amplification circuits.

As an example, the flow cytometer 10 includes a measurement unit 65 equipped with the configuration illustrated in FIG. 3 including the light source 124, the flow cell 20, and the light receiving elements 100A to 100F, and as illustrated in FIG. 5, the amplification units 130A to 130F, the A/D conversion units 131A to 131F, the signal processing unit 63, and a temperature sensor 22 to be described later. The measurement unit 65 optically measures particles in the particle-containing liquid passing through the flow cell 20 in accordance with a measurement condition received by a communication unit 64 to be described later. The measurement includes detection of the optical information of the particle-attributable light by the light receiving elements 100A to 100F, and storage of the detection signals output from the light receiving elements 100A to 100F. The measurement also includes processing performed by the signal processing unit 63 to be described later, such as generation of a result of measurement of the number of particles or the like by using the stored detection signals. The detection signals output from the light receiving elements 100A to 100F include signals output from the A/D conversion units 131A to 131F through the amplification units 130A to 130F.

As illustrated in FIG. 1, the flow cytometer 10 includes the flow cytometer body 13, and the information processing device 14 connected with the flow cytometer body 13. The configuration including the light source 124, the flow cell 20, and the light receiving elements 100A to 100F, which is illustrated in FIG. 2, and the amplification units 130A to 130F, and the A/D conversion units 131A to 131F in the measurement unit 65 are disposed in the flow cytometer body 13. The signal processing unit 63 is disposed in the information processing device 14. When the flow cytometer 10 includes no information processing device 14, the signal processing unit 63 may be disposed in the flow cytometer body 13. The flow cytometer 10 also includes a controller that controls a pump, a motor, or the like (not illustrated) for causing the particle-containing liquid to pass through the flow cell 20 to perform measurement, but the controller may be achieved by the signal processing unit 63, and may be separately disposed in the information processing device 14 or the flow cytometer body 13.

[Measurement Condition]

To set a measurement condition in accordance with measurement items before measurement, the flow cytometer 10 receives a measurement condition included in the measurement order, for example, from the electronic medical record system 50 illustrated in FIG. 1. The flow cytometer 10 may receive a measurement condition from an external server (not illustrated). FIG. 4 exemplarily illustrates information included in the received measurement condition when the particle-attributable light is fluorescence. The measurement condition includes basic information on measurement (hereinafter referred to as "basic measurement information"), information on adjustment of the detection sensitivity for detecting the optical information (hereinafter referred to as "detection sensitivity adjustment related information"), information on correction of the detected optical information, gating related information for setting a selected particle region based on the optical information (hereinafter referred to as "gating related information"), and a formula used for temperature correction to be described later.

The basic measurement information includes basic information, measurement information, and a threshold. The basic information includes identification information (referred to as "measurement condition ID" in FIG. 4) for specifying the kind of measurement condition and a measurement condition name. The measurement information includes the analysis amount of the specimen aspirated into the flow cytometer, a flow rate indicating a flow speed at which particles flow into the flow cytometer, and the dilution ratio of the specimen aspirated into the flow cytometer. The threshold is also called a sensing level, and is the lower limit set value of the optical information detected as a particle. The light receiving elements 100A to 100F each set the threshold for the light attributable to particles. For example, the threshold can be set in the numerical value range of 0 to 1000 in accordance with the intensity of light. When the threshold is set to be 50, light having an intensity of 50 or higher is detected as a particle.

The detection sensitivity adjustment related information includes at least one of a value indicating the degree of amplification of the output voltage of each of the light receiving elements 100A to 100F and the value of voltage applied to each of the light receiving elements 100A to 100F. For example, the detection sensitivity adjustment related information includes an amplification value for adjusting the degree of amplification at each of amplification circuits connected with the light receiving elements 100A and 100B and a PMT voltage value for adjusting voltage applied to each of the light receiving elements 100C to 100F. The detection sensitivity adjustment related information may include only any one of the amplification value and the PMT voltage value. When amplification circuits are connected with the light receiving elements 100C to 100F, the detection sensitivity adjustment related information may include an amplification value adjusting the degree of amplification at each amplification circuit.

The information on correction of the detected optical information includes information on the distribution amount of light wavelengths not to be detected, which is included in the optical information detected by the light receiving elements 100A to 100F. When two or more kinds of light emitted from particles and having different peak wavelengths are detected at single measurement, the wavelength regions of the two or more kinds of light partially overlap with each other in some cases. As a result, uniqueness of light detection decreases in some cases due to leakage into one kind of light to be detected from another kind of light not to be detected. The wavelength distribution and quantity of light are collectively referred to as a light wavelength distribution amount, and the wavelength distribution and light quantity of leakage light are collectively referred to as a light wavelength distribution amount not to be detected. The light receiving elements 100C to 100F cannot selectively receive an overlapping part of two or more light wavelength regions, and thus what is called fluorescence correction is performed to extract only optical information obtained from fluorescence to be detected by removing an electric signal attributable to fluorescence not to be detected from an electric signal of each of the light receiving elements 100C to 100F. Information on the light wavelength distribution amount not to be detected, which is included in the detected optical information is indicated as a fluorescence correction value in FIG. 4 and used for the fluorescence correction. The simplest fluorescence correction value is the light wavelength distribution amount of fluorescence not to be detected, which is to be subtracted from the light wavelength distribution amount of fluorescence to be detected. For example, two kinds of fluorescence having different peak wavelengths are referred to as fluorescence 1 and fluorescence 2. The fluorescence correction value of fluorescence 1 is 0.0 when light wavelength distribution does not overlap between fluorescence 1 and fluorescence 2 and no fluorescence correction is needed. When light distribution wavelength overlapping is observed at simultaneous measurement of fluorescence 1 and fluorescence 2 and the amount of the light wavelength distribution overlapping is 27.5%, the fluorescence correction value is set to be 27.5 to subtract 27.5% of a fluorescence distribution amount attributable to fluorescence 2 from the fluorescence distribution amount of fluorescence 1.

The gating related information includes information on distribution setting on a distribution diagram of the light attributable to particles. For one measurement item or each of two or more measurement items, the flow cytometer produces a distribution diagram such as a scattergram or a histogram of the light attributable to particles from detected optical information. The scattergram illustrates distribution of the light attributable to particles on the two axes of an X axis and a Y axis for two measurement items. The histogram illustrates the strength of light and the number of particles for one measurement item. Gating is selection of a certain distribution region in accordance with a measurement item in each distribution diagram to perform appropriate measurement in accordance with the measurement item. More specifically, the gating is setting of information described below.

The information on distribution setting on the distribution diagram of the light attributable to particles includes information on a scattergram, information on a histogram, and information on a gate. The information on a scattergram is information for producing a scattergram and includes a scattergram name as the name of the produced scattergram, a higher-level gate, an X-axis channel (also referred to as X-axis ch) indicating a photodiode receiving light representing a first measurement item, the name of the X-axis channel, a Y-axis channel (also referred to as Y-axis ch) indicating a photodiode receiving light representing a second measurement item, and the name of the Y-axis channel. The information on a histogram is information for producing a histogram and includes a histogram name, a higher-level gate, an X-axis channel indicating a photodiode receiving light representing a measurement item, and the name of the X-axis channel. The higher-level gate is a gate of a scattergram produced first when two or more gates are used to produce scattergrams corresponding to the respective gates. The information on a gate is used to determine each particle region selected from a scattergram or a histogram and includes a gate name as the name of a selected gate, position information indicating the position of the gate, a color provided to the wavelength or wavelength region of received light on the display unit, a measurement item name, the upper limit value of the intensity of received light, the lower limit value of the intensity of received light, and a result value type when an analysis result is displayed. The result value type includes various statistically processed values of a result and is, for example, a particle total number, an average value, a variation coefficient, a ratio relative to the whole, or a mode value.

The number of produced scattergrams and histograms differs depending on each measurement item. Thus, a plurality of pieces of the information on a scattergram, a plurality of pieces of the information on a histogram, and a plurality of pieces of the information on a gate are included in accordance with the number of produced scattergrams and histograms in some cases. The information on distribution setting on the distribution diagram of the light attributable to particles may include information on a dot plot.

[Information Processing System of Flow Cytometer]

FIG. 5 is a diagram illustrating an exemplary information processing system of the flow cytometer according to one or more embodiments. FIG. 5 illustrates the configuration of the information processing system of the flow cytometer 10, which includes, as an example, an input unit 60, a condition input unit 61, the display unit 62, the signal processing unit 63, and the communication unit 64. The signal processing unit 63 acquires, through the amplification units 130A to 130F and the A/D conversion units 131A to 131F, the detection signals output from the light receiving elements 100A to 100F. The information processing system also includes the temperature sensor 22 that detects the temperature of the particle-containing liquid and outputs a temperature detection signal converted into an electric signal. The signal processing unit 63 may acquire the temperature detection signal from the temperature sensor 22 through a temperature detection circuit 132 and an A/D conversion unit 133.

The input unit 60 (reading unit) is achieved by a bar code reader, and reads a bar code (code) provided to a reagent container in which a reagent to be added to a sample is stored. The input unit 60 outputs bar code information to the signal processing unit 63. The code is not limited to a bar code as a one-dimensional code, but may include a QR code (registered trademark) as a two-dimensional code or include another code. The input unit 60 is achieved by, for example, at least one of a keyboard, a mouse, and a touch panel, and receives inputting for changing a measurement item or the like from a user operating the flow cytometer 10.

The condition input unit 61 is achieved by, for example, at least one of a keyboard, a mouse, and a touch panel, and receives inputting of a measurement condition from the user operating the flow cytometer 10.

The display unit 62 (output unit) is achieved by, for example, a monitor, and outputs measurement data based on the acquired reagent information in a manner that enables identifying, distinguishing, or recognizing whether the measurement data is measurement data of particles contained in the measurement specimen prepared through addition of the in-vitro diagnostics reagent. As described above, the measurement data is output as data of a scattergram, a histogram, a dot plot, or the like illustrating, for example, a particle distribution status. The display unit 62 may further display a measurement item and a measurement condition.

The input unit 60, the condition input unit 61, and the display unit 62 are disposed in the information processing device 14 connected with the flow cytometer body 13, but may be disposed in the flow cytometer body 13.

The communication unit 64 is achieved by, for example, a communication device used to communicate with the electronic medical record system 50 through the communication network N1 illustrated in FIG. 1.

As an example, the signal processing unit 63 includes a memory 82 used as a work area of data processing, a storage unit 83 in which a computer program and processing data are recorded, a central processing unit (CPU) 81 that performs data processing to be described later, and a bus 84 through which data is transmission between the components. As an example, the signal processing unit 63 also includes interface units (denoted by "I/F units" in FIGS. 5) 85 and 86 through which data inputting and outputting are performed with the units 60, 61, 62, and 64 connected with the signal processing unit 63, to which the detection signals output from the light receiving elements 100A to 100F are input through the amplification units 130A to 130F and the A/D conversion units 131A to 131F, and to which the temperature detection signal from the temperature sensor 22 is input through the temperature detection circuit 132 and the A/D conversion unit 133.

In the following description, unless otherwise stated, processing performed by the signal processing unit 63 means processing performed by the CPU 81 of the signal processing unit 63 in reality. The CPU 81 temporarily stores necessary data (such as intermediate data being processed) in the memory 82 as a work area, and records data to be stored for a long period in the storage unit 83 as appropriate.

Figure 6:
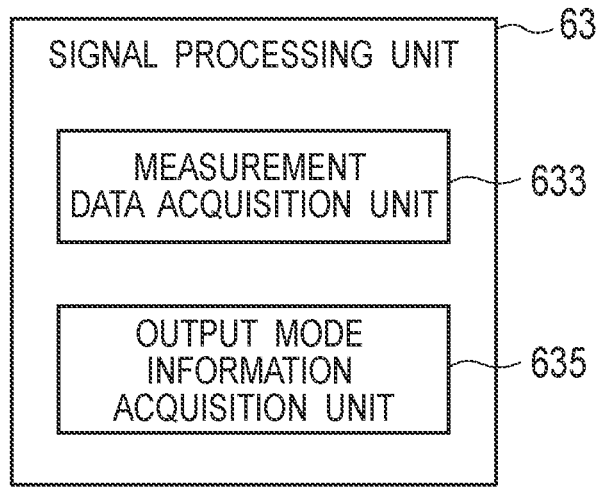
FIG. 6 is a diagram illustrating an exemplary functional block of an information processing unit according to one or more embodiments.

FIG. 6 is a diagram illustrating an exemplary functional block of an information processing unit according to one or more embodiments. As illustrated in FIG. 6, the signal processing unit 63 executes a computer program stored in the storage unit 83 or the memory 82 illustrated in FIG. 5 to achieve, as an example, a measurement data acquisition unit 633 that measures particles contained in a measurement specimen prepared by adding a reagent to a sample to acquire measurement data of the particles, and an output mode information acquisition unit 635 that acquires reagent information that enables identifying, distinguishing, or recognizing whether the reagent is an in-vitro diagnostics reagent for use in in-vitro diagnosis. As an example, the signal processing unit 63 may also function as an order information acquisition unit that acquires order information including one or a plurality of measurement items from the electronic medical record system 50 illustrated in FIG. 1. The signal processing unit 63 controls operation of each component connected with the signal processing unit 63.

[Measurement Data Output Processing]

Figure 7:
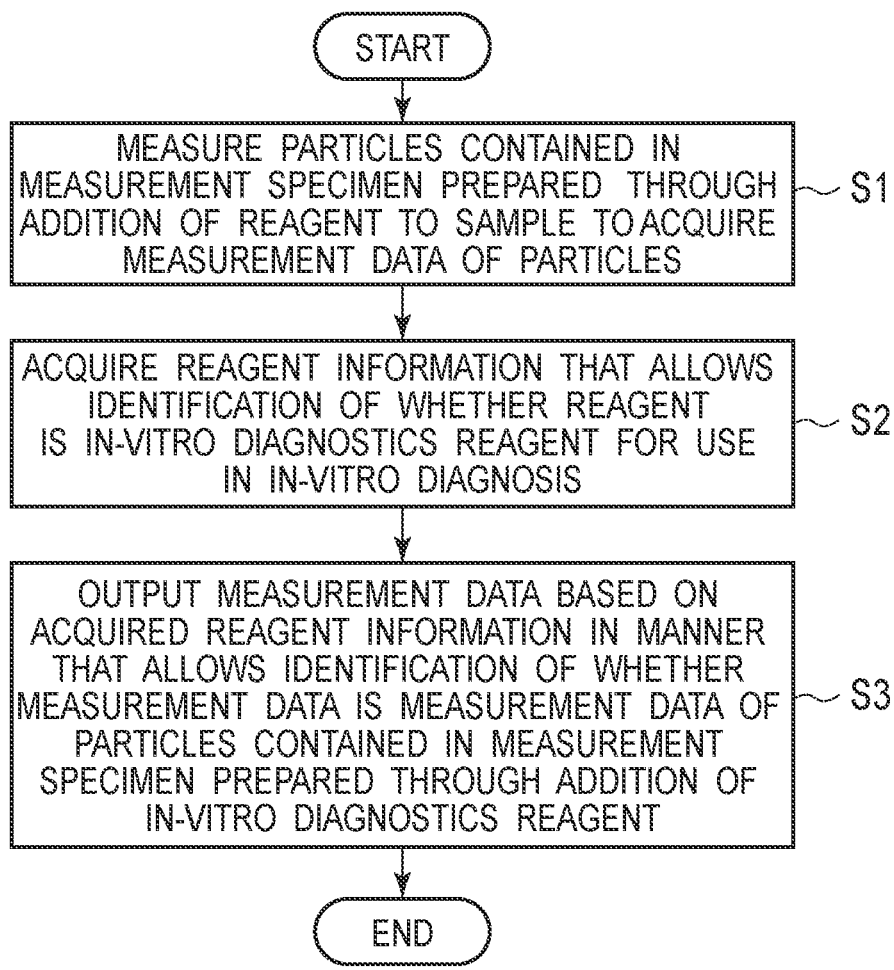
FIG. 7 is a diagram illustrating exemplary measurement data output processing performed by a specimen analysis system according to one or more embodiments.

FIG. 7 is a diagram illustrating exemplary measurement data output processing performed by the specimen analysis system according to one or more embodiments.

(Step S1)

The flow cytometer 10 illustrated in FIG. 1 measures particles contained in a measurement specimen prepared by adding a reagent to a sample to acquire measurement data of the particles. Specifically, the flow cytometer 10 acquires measurement order including one or a plurality of measurement items from the electronic medical record system 50. The pretreatment device 15 of the flow cytometer 10 adds the reagent to the sample in accordance with the one or plurality of measurement items included in the measurement order. With this configuration, the measurement specimen to be measured can be appropriately prepared through pretreatment of main measurement treatment for acquisition of the measurement data.

The pretreatment device 15 provides the prepared measurement specimen to the flow cytometer 10 together with information on the measurement items. Then, the flow cytometer 10 measures particles contained in the measurement specimen prepared through addition of the reagent as the pretreatment, thereby acquiring measurement data of the particles. With this configuration, particles contained in the sample can be measured in accordance with one or a plurality of measurement items included in order information, and thus measurement results in accordance with the measurement items can be acquired.

(Step S3)

The flow cytometer 10 acquires reagent information that enables identifying, distinguishing, or recognizing whether the reagent is an in-vitro diagnostics reagent for use in in-vitro diagnosis.

Figures 8, 9:
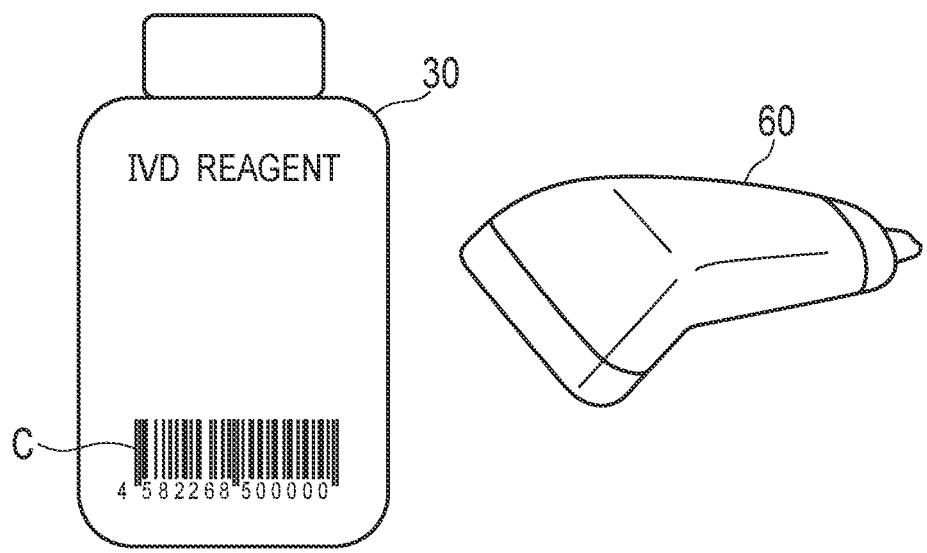
FIG. 8 is a diagram illustrating exemplary processing performed by a reading unit according to one or more embodiments to read a code attached to a reagent container in which a reagent is stored.
FIG. 9 is a diagram illustrating an exemplary information table according to one or more embodiments in which identification information of a sample and reagent information of a reagent added to the sample are recorded in association with each other.

FIG. 8 is a diagram illustrating exemplary processing performed by the reading unit according to one or more embodiments to read a code attached to a reagent container in which the reagent is stored. As illustrated in FIG. 8, the input unit 60 (reading unit) of the flow cytometer 10 illustrated in FIG. 5 reads a bar code C (code) attached to a reagent container 30 in which an IVD reagent is stored. Then, the output mode information acquisition unit 635 of the flow cytometer 10 illustrated in FIG. 6 acquires reagent information of the reagent, which is included in the read bar code. With this configuration, the reagent information can be reliably and easily acquired.

The output mode information acquisition unit 635 may acquire reagent information input by the user through, for example, a keyboard as the input unit 60. The acquired reagent information is recorded in the storage unit 83 illustrated in FIG. 5.

FIG. 9 is a diagram illustrating an exemplary information table according to one or more embodiments in which identification information of a sample and reagent information of a reagent added to the sample are recorded in association with each other. As illustrated in FIG. 9, the storage unit 83 illustrated in FIG. 5 stores a patient name, identification information (ID) of a parent sample, identification information (ID) of a child sample, and the reagent information in association with each other. For example, the reagent information may include reagent information that enables identifying, distinguishing, or recognizing whether the reagent is an in-vitro diagnostics reagent (IVD reagent), a research use only reagent (RUO reagent), or an analyte specific reagent (ASR). With this configuration, it is possible to appropriately identify whether the reagent added to the sample is an IVD reagent, a RUO reagent, or an ASR. The storage unit 83 may further record panel information of samples. The panel information includes information (for example, plot representation) indicating an output form at outputting of measurement data based on the samples, and setting information of an output parameter, a threshold, and the like. The storage unit 83 may further store facility identification information to identify a facility at which a clinical test using a flow cytometer body 13 illustrated in FIG. 1 is performed.

(Step S5)

The measurement data is output based on the acquired reagent information in a manner that enables identifying, distinguishing, or recognizing whether the measurement data is measurement data of particles contained in the measurement specimen prepared through addition of the in-vitro diagnostics reagent.

Figure 10:
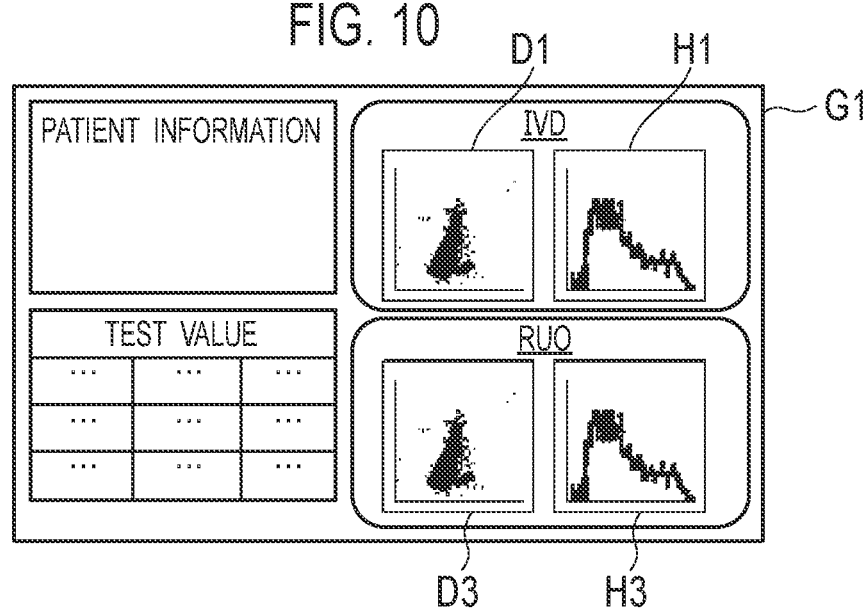
FIG. 10 is a diagram illustrating an exemplary electronic medical record outputting screen on an output unit according to one or more embodiments.

FIG. 10 is a diagram illustrating an exemplary electronic medical record outputting screen on the output unit according to one or more embodiments. As illustrated in FIG. 10, the output unit 70 of the doctor terminal device 7, the output unit 90 of a laboratory technician terminal 9, which are illustrated in FIG. 1, or the output unit 62 of the flow cytometer 10 illustrated in FIG. 5 (hereinafter referred to as "each output unit") may output, on an identical or same screen or an identical or same sheet, measurement data of particles contained in a measurement specimen prepared through addition of an IVD reagent and measurement data of particles contained in a measurement specimen prepared through addition of a RUO reagent other than the IVD reagent. Specifically, an electronic medical record including patient information, the test value of a sample associated with a patient, a dot plot D1 and a histogram H1 corresponding to measurement data of particles contained in a measurement specimen prepared through addition of an IVD reagent, and a dot plot D3 and a histogram H3 corresponding to measurement data of particles contained in a measurement specimen prepared through addition of a RUO reagent are output on an electronic medical record outputting screen G1 on each output unit. With this configuration, for example, screen switching is not needed to check the measurement data based on the IVD reagent and the measurement data based on the RUO reagent other than the IVD reagent, and thus it is possible to improve convenience for the user.

Each output unit may output, in different regions on an identical or same screen or an identical or same sheet, measurement data of particles contained in a measurement specimen prepared through addition of an IVD reagent and measurement data of particles contained in a measurement specimen prepared through addition of a RUO reagent other than the IVD reagent. With this configuration, it is possible to easily identify the measurement data based on the IVD reagent and the measurement data based on the RUO reagent other than the IVD reagent.

Each output unit may output, in different output forms, measurement data of particles contained in a measurement specimen prepared through addition of an IVD reagent and measurement data of particles contained in a measurement specimen prepared through addition of a RUO reagent other than the IVD reagent. For example, the output form of the measurement data based on the IVD reagent is enhanced as compared to the output form of the measurement data of based on the RUO reagent. Specifically, the output size of the measurement data based on the IVD reagent is increased as compared to that of the measurement data of based on the RUO reagent, or the measurement data based on the IVD reagent is output in red whereas the measurement data of based on the RUO reagent is output in black. With this configuration, it is possible to easily identify the measurement data based on the IVD reagent and the measurement data based on the RUO reagent other than the IVD reagent without distinguishing the output regions thereof.

Alternatively, the measurement data based on the IVD reagent and the measurement data based on the RUO reagent other than the IVD reagent may be output in different output forms while the output regions thereof are distinguished. With this configuration, it is possible to more reliably and more easily identify both data.

Each output unit may output measurement data based on reagent information stored in the storage unit 83 illustrated in FIG. 5, in a manner that enables identifying, distinguishing, or recognizing whether the measurement data is measurement data of particles contained in a measurement specimen prepared through addition of an ASR. With this configuration, when the measurement data is output, it is possible to easily identify whether the measurement data is based on the ASR.

When measurement data is output for each of a plurality of samples, each output unit may output the measurement data based on identification information of each sample and reagent information of a reagent added to the sample, which are stored in the storage unit 83, in a manner that enables identifying, distinguishing, or recognizing whether the reagent added to each sample is an IVD reagent. With this configuration, when measurement data is output for each of a plurality of sample, it is possible to easily identify whether a reagent added to each sample is an IVD reagent.

As described above, the storage unit 83 illustrated in FIG. 5 may further store facility identification information to identify a facility at which a clinical test using the flow cytometer 10 illustrated in FIG. 1 is performed. Each output unit may output measurement data based on the facility identification information stored in the storage unit 83 in a manner that enables identifying, distinguishing, or recognizing whether the measurement data is measurement data of particles contained in a measurement specimen prepared through addition of an IVD reagent. Specifically, a result of measurement using an analyte-specific reagent (ASR) at a clinical test facility (facility certified by Clinical Laboratory Improvement Amendments (CLIA)) that satisfies a certain condition can be output as measurement data based on an IVD reagent. The facility identification information includes, for example, information indicating whether the facility is certified by CLIA. With this configuration, it is possible to easily identify whether measurement data obtained at a particular facility that satisfies a certain condition is measurement data based on an IVD reagent.

Figure 11:
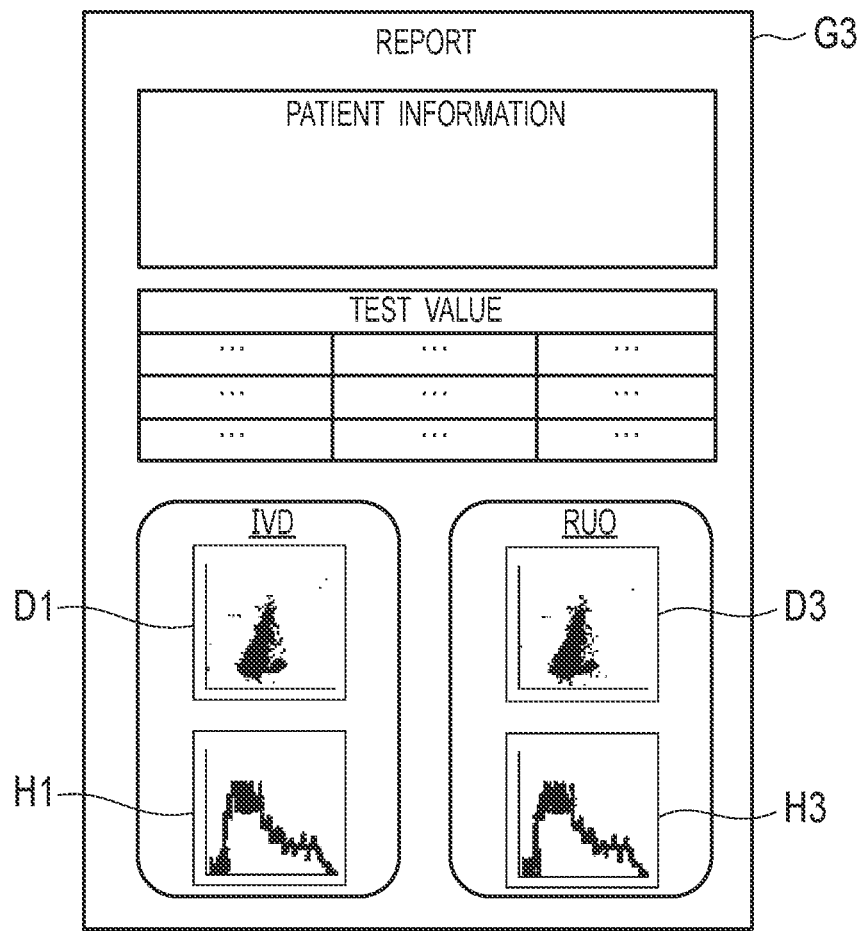
FIG. 11 is a diagram illustrating an exemplary report outputting screen on an output unit according to one or more embodiments.

FIG. 11 is a diagram illustrating an exemplary report outputting screen on the output unit of the doctor terminal device according to one or more embodiments. As illustrated in FIG. 11, measurement data of particles contained in a measurement specimen prepared through addition of an IVD reagent and measurement data of particles contained in a measurement specimen prepared through addition of a RUO reagent other than the IVD reagent may be output in the format of "report" on an identical or same screen or an identical or same sheet. Specifically, a report including patient information, the test value of a sample associated with a patient, a dot plot D1 and a histogram H1 corresponding to measurement data of particles contained in a measurement specimen prepared through addition of an IVD reagent, and a dot plot D3 and a histogram H3 corresponding to measurement data of particles contained in a measurement specimen prepared through addition of a RUO reagent may be output on a report outputting screen G3 on each output unit.

Figure 12A:
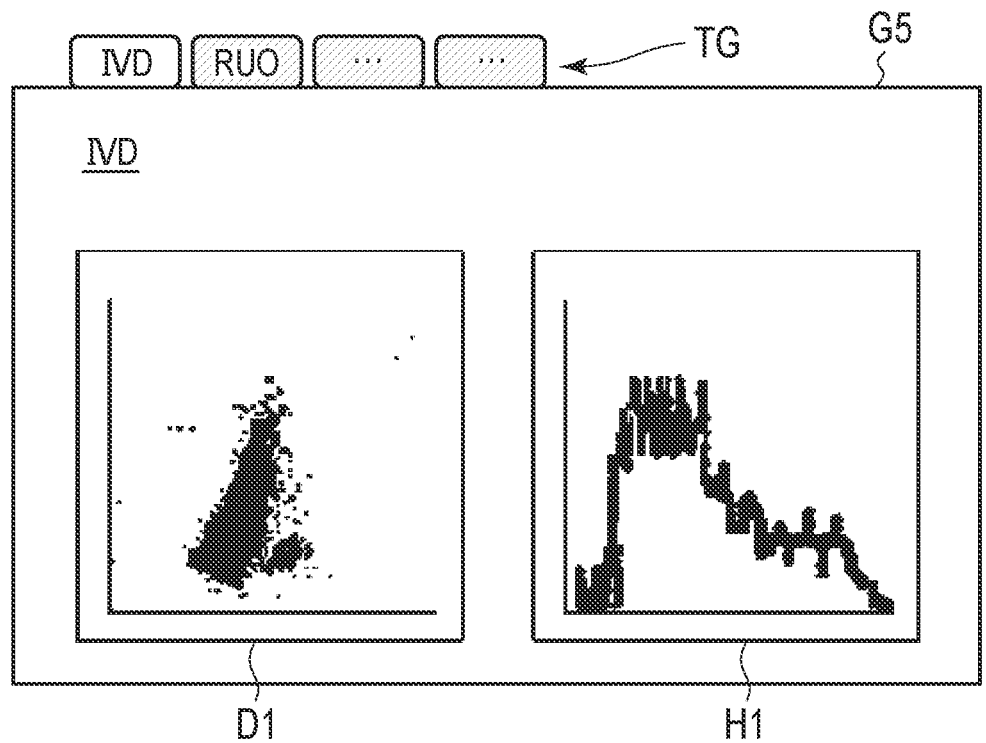
FIG. 12A and FIG. 12B are diagrams each illustrating an exemplary measurement data outputting screen on an output unit according to one or more embodiments.
Figure 12B:
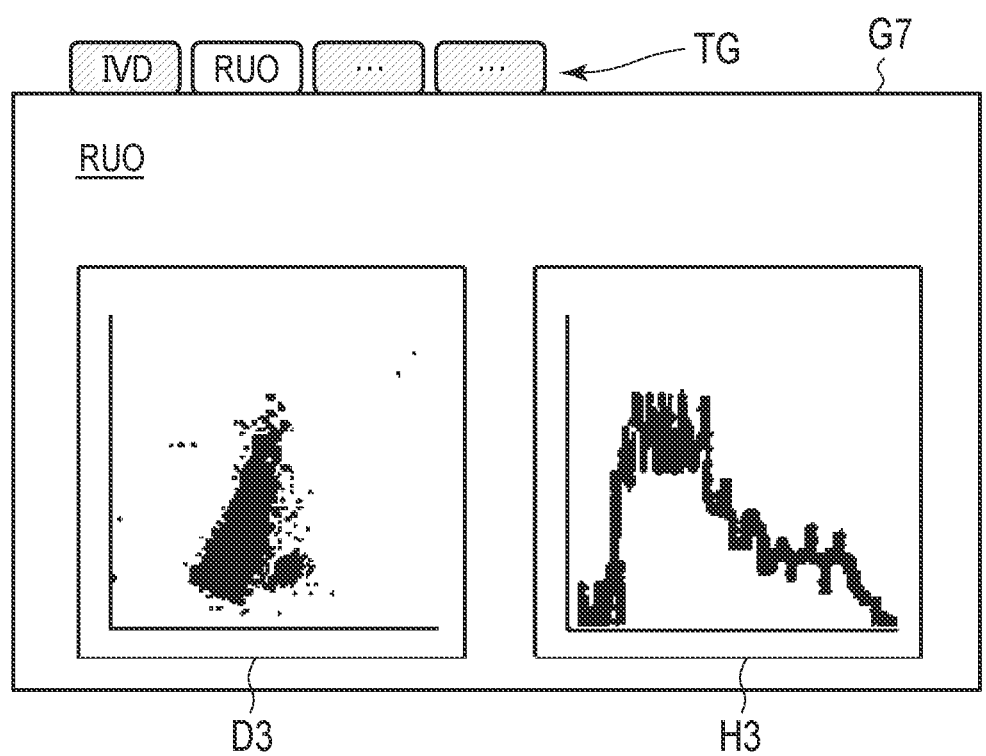

FIG. 12A and FIG. 12B are diagrams each illustrating an exemplary measurement data outputting screen on the output unit of the doctor terminal device according to one or more embodiments. As illustrated in FIG. 12A and FIG. 12B, upon selection of a tag TG by the user, each output unit may display, in a switching manner, a screen G5 (refer to FIG. 12A) on which a dot plot D1 and a histogram H1 corresponding to measurement data of particles contained in a measurement specimen prepared through addition of an IVD reagent are output, and a screen G7 (refer to FIG. 12B) on which a dot plot D3 and a histogram H3 corresponding to measurement data of particles contained in a measurement specimen prepared through addition of a RUO reagent other than the IVD reagent are output. With this configuration, the measurement data based on the IVD reagent and the measurement data based on the RUO reagent other than the IVD reagent are output on different screens, and thus it is possible to reliably identify both data.

As described above, according to one or more embodiments, the specimen analysis system 1 outputs acquired measurement data based on acquired reagent information in a manner that enables identifying, distinguishing, or recognizing whether the measurement data is measurement data of particles contained in a measurement specimen prepared through addition of an IVD reagent for use in in-vitro diagnosis. With this configuration, it is possible to prevent a doctor or the like from performing false diagnosis and reporting a false analysis result, and thus it is possible to provide a report in a format in accordance with the reagent information, and it is possible to significantly improve convenience for the user. In addition, it is possible to automatically produce a report in accordance with the reagent information, and thus it is not needed to educate and train an experienced and skilled technical expert to perform report production work and it is not needed to employ an experienced and skilled technical expert. Accordingly, it is possible to establish a specimen analysis system for which no special technical expert is needed. In addition, it is possible to produce a report in accordance with the reagent information, and thus it is possible to appropriately output a report including the measurement data when an optional reagent is selected by the user.

Other Embodiments

The above-described embodiments are intended to facilitate understanding of the present invention and should not be understood to limit the present invention. One or more embodiments may be changed and modified (for example, embodiments may be combined, or part of the configuration of each embodiment may be omitted) without departing from the scope of the invention. In addition, one or more embodiments include equivalents thereof.

For example, the measurement data acquisition unit 633 of the flow cytometer 10 illustrated in FIG. 5 may acquire measurement data obtained from a measurement device other than the flow cytometer 10, and each output unit may output the measurement data obtained from the measurement device other than the flow cytometer 10. With this configuration, it is possible to collectively output not only measurement data obtained from the flow cytometer 10 but also measurement data obtained from a measurement device other than the flow cytometer 10.

Each output unit may output the measurement data obtained from measurement device other than the flow cytometer 10, as measurement data other than measurement data of particles contained in a measurement specimen prepared through addition of an IVD reagent. With this configuration, when measurement data obtained from a measurement device other than the flow cytometer 10 is output, it is possible to easily identify the measurement data.

Measurement data obtained from a measurement device other than the flow cytometer 10 may include measurement data obtained through at least one of a hematology test, a blood smear test, an image diagnosis, a blood coagulation test, an immunity test, a biochemical test, a urine test, and a gene test. With this configuration, measurement data obtained by various test methods can be acquired from the measurement device other than the flow cytometer 10.

Measurement data obtained from a measurement device other than the flow cytometer 10 may be data acquired from any one of the HIS 2, the LIS 4, and a test information management system. With this configuration, measurement data can be acquired from another system other than the flow cytometer 10.

Each output unit may output a result of accuracy control of the flow cytometer 10 as data other than measurement data of particles contained in a measurement specimen prepared through addition of an IVD reagent. The result of accuracy control is a result of management to correct a measurement result by maintaining a measurement instrument and improving a measurement method. With this configuration, the result of accuracy control of the flow cytometer 10 can be included in a report, which assures the reliability of measurement data.

The invention claimed is:
1. A specimen analysis system, comprising:
a flow cytometer configured to measure particles contained in a measurement specimen prepared by combining a reagent and a sample;
a display; and a processor programmed to perform operations comprising:
acquiring measurement data of particles obtained from the flow cytometer;
reading a code attached to a reagent container in which the reagent is stored;
identifying a type of the reagent on the basis of the code read from the reagent container, the type being selected at least from (i) IVD (in-vitro diagnostic) reagent and (ii) RUO (research use only) reagent;
acquiring at least first and second measurement data that are derived from first and second measurement specimens from a single patient, the first measurement specimen being prepared with IVD reagent and the second measurement specimen being prepared with RUO reagent; and
displaying, on the display, the first measurement data and the second measurement data in in divided regions of a display screen.

2. The specimen analysis system according to claim 1, wherein the processor is programmed to perform operations further comprising:
acquiring output mode information indicating an output form of the measurement data; and
outputting the measurement data in the output form in accordance with the output mode information, and
the output mode information comprises information whether: the measurement data comprises only a test value of the particles contained in the measurement specimen; or the measurement data comprises, in addition to the test value, at least one of: particle data comprising optical information of the particles contained in the measurement specimen, and data on a particle distribution diagram of the particles generated based on the particle data, and
the measurement data is output, based on the information, in a distinguishable manner whether the measurement data comprises only the test value or comprises, in addition to the test value, the at least one of the particle data comprising the optical information of the particles contained in the measurement specimen and the data on the particle distribution diagram of the particles generated based on the particle data.

3. The specimen analysis system according to claim 1, wherein the processor is programmed to perform operations further comprising:
acquiring output mode information indicating an output form of the measurement data; and
outputting the measurement data in the output form in accordance with the output mode information, and
the output mode information comprises reagent information whether the reagent comprises an in-vitro diagnostics reagent for use in in-vitro diagnosis, and
the measurement data is output, based on the reagent information, in a distinguishable manner whether the measurement data comprises measurement data of particles contained in a measurement specimen prepared by combining the in-vitro diagnostics reagent with the sample.

4. The specimen analysis system according to claim 3, further comprising a storage unit that stores identification information of the sample and the reagent information of the reagent added to the sample in association with each other, wherein,
the measurement data is output, based on the identification information and the reagent information, in a distinguishable manner whether the reagent added to the sample comprises the in-vitro diagnostics reagent.

5. The specimen analysis system according to claim 3, wherein the measurement data of the particles contained in the measurement specimen prepared by combining the in-vitro diagnostics reagent with the sample and measurement data of particles contained in a measurement specimen prepared by combining a reagent other than the in-vitro diagnostics reagent with the sample are output on a same screen of the display or on a same sheet.

6. The specimen analysis system according to claim 3, wherein the measurement data of the particles contained in the measurement specimen prepared by combining the in-vitro diagnostics reagent with the sample and measurement data of particles contained in a measurement specimen prepared by combining a reagent other than the in-vitro diagnostics reagent with the sample are output in different regions on a same screen of the display or on a same sheet.

7. The specimen analysis system according to claim 3, wherein a screen of the display on which the measurement data of the particles contained in the measurement specimen prepared by combining the in-vitro diagnostics reagent with the sample is output and a screen of the display on which measurement data of particles contained in a measurement specimen prepared by combining a reagent other than the in-vitro diagnostics reagent with the sample is output are output in a switching manner.

8. The specimen analysis system according to claim 3, wherein the measurement data of the particles contained in the measurement specimen prepared by combining the in-vitro diagnostics reagent with the sample and measurement data of particles contained in a measurement specimen prepared by combining a reagent other than the in-vitro diagnostics reagent with the sample are output in different output forms.

9. The specimen analysis system according to claim 3, further comprising a storage unit that stores facility identification information to identify a facility in which a clinical test using the flow cytometer is performed, wherein
the measurement data, based on the facility identification information, in a distinguishable manner whether the measurement data comprises the measurement data of the particles contained in the measurement specimen prepared by combining the in-vitro diagnostics reagent with the sample.

10. The specimen analysis system according to claim 3, wherein the reagent information comprises reagent information whether the reagent comprises the in-vitro diagnostics reagent or an analyte specific reagent (ASR).

11. The specimen analysis system according to claim 10, wherein the measurement data is output, based on the reagent information, in a distinguishable manner whether the measurement data comprises measurement data of particles contained in a measurement specimen prepared by combining the ASR with the sample.

12. The specimen analysis system according to claim 3, further comprising a pretreatment device configured to prepare the measurement specimen by combining the reagent with the sample.

13. The specimen analysis system according to claim 3, wherein the processor is programmed to perform operations further comprising
acquiring measurement data obtained from a measurement device other than the flow cytometer, and
outputting the measurement data obtained from the measurement device.

14. The specimen analysis system according to claim 13, wherein the processor is programmed to perform operations such that outputting the measurement data further comprises outputting the measurement data obtained from the measurement device as measurement data other than the measurement data of the particles contained in the measurement specimen prepared by combining the in-vitro diagnostics reagent with the sample.

15. The specimen analysis system according to claim 13, wherein the measurement data obtained from the measurement device comprises measurement data obtained through at least one selected from a group consisting of a hematology test, a blood smear test, an image diagnosis, a blood coagulation test, an immunity test, a biochemical test, a urine test, and a gene test.

16. The specimen analysis system according to claim 13, wherein the measurement data obtained from the measurement device comprises data acquired from at least one selected from a group consisting of a hospital information system that supports hospital operations, a clinical laboratory information system that supports clinical test operations, and a test information management system.

17. The specimen analysis system according to claim 3, wherein a result of accuracy control of the flow cytometer is output as data other than the measurement data of the particles contained in the measurement specimen prepared by combining the in-vitro diagnostics reagent with the sample.

18. A specimen analysis method which is executed by a computer, the method comprising:
    acquiring measurement data of particles obtained from a flow cytometer measuring the particles contained in a measurement specimen prepared by combining a reagent with a sample;
    reading a code attached to a reagent container in which the reagent is stored;
    identifying a type of the reagent on the basis of the code read from the reagent container, the type being selected at least from (i) IVD (in-vitro diagnostic) reagent and (ii) RUO (research use only) reagent;
    acquiring at least first and second measurement data that are derived from first and second measurement specimens from a single patient, the first measurement specimen being prepared with IVD reagent and the second measurement specimen being prepared with RUO reagent,
    displaying, on a display, the first measurement data and the second measurement data in divided regions of a display screen.

19. The specimen analysis method according to claim 18, further comprising:
    acquiring output mode information indicating an output form of the measurement data; and
    outputting the measurement data in the output form in accordance with the output mode information, wherein
    the output mode information comprises information whether: the measurement data comprises only a test value of the particles contained in the measurement specimen; or the measurement data comprises, in addition to the test value, at least one of: particle data comprising optical information of the particles contained in the measurement specimen, and data on a particle distribution diagram of the particles generated based on the particle data, and
    the outputting comprises outputting the measurement data, based on the information, in a distinguishable manner whether the measurement data comprises only the test value or comprises, in addition to the test value, the at least one of the particle data comprising the optical information of the particles contained in the measurement specimen and the data on the particle distribution diagram of the particles generated based on the particle data.

20. The specimen analysis method according to claim 18, further comprising:
    acquiring output mode information indicating an output form of the measurement data; and
    outputting the measurement data in the output form in accordance with the output mode information, wherein
    the output mode information comprises reagent information whether the reagent comprises an in-vitro diagnostics reagent for use in in-vitro diagnosis, and
    the outputting comprises outputting the measurement data, based on the reagent information, in a distinguishable manner whether the measurement data comprises measurement data of particles contained in a measurement specimen prepared by combining the in-vitro diagnostics reagent with the sample.

21. A specimen analysis system, comprising:
    a flow cytometer configured to measure particles contained in a measurement specimen prepared by combining a reagent with a sample;
    a display; and
    a processor programmed to perform operations comprising:
    acquiring measurement data of particles from the flow cytometer;
    reading a code attached to a reagent container in which the reagent is stored;
    identifying, from the code read by the reading unit, whether the reagent comprises an in-vitro diagnostics reagent for use in in-vitro diagnosis, or a research use only reagent;
    acquiring at least first and second measurement data that are derived from first and second measurement specimens from a single patient, the first measurement specimen being prepared with a reagent for use in in-vitro diagnosis and the second measurement specimen being prepared with a reagent for research use only; and
    displaying, on the display, the first measurement data and the second measurement data in divided regions of a display screen.

22. A specimen analysis method, comprising:
    acquiring measurement data of particles by measuring, using a flow cytometry, the particles contained in a measurement specimen prepared by combining a reagent with a sample;
    reading a code attached to a reagent container in which the reagent is stored;
    identifying from the code, whether the reagent comprises an in-vitro diagnostics reagent for use in in-vitro diagnosis, or a research use only reagent;
    acquiring at least first and second measurement data that are derived from first and second measurement specimens from a single patient, the first measurement specimen being prepared with a reagent for use in in-vitro diagnosis and the second measurement specimen being prepared with a reagent for research use only, and
    displaying, on a display, the first measurement data and the second measurement data in divided regions of a display screen.

23. The specimen analysis method according to claim 22, further comprising outputting the measurement data based on the reagent information, wherein the outputting comprises outputting the measurement data, based on the reagent information, in a distinguishable manner whether the measurement data comprises measurement data of particles contained in a measurement specimen prepared by combining the in-vitro diagnostics reagent with the sample.

* * * * *